(12) United States Patent
Takabayashi et al.

(10) Patent No.: US 7,672,544 B2
(45) Date of Patent: Mar. 2, 2010

(54) OPTICAL FIBER SENSOR

(75) Inventors: Masakazu Takabayashi, Tokyo (JP);
Kiichi Yoshiara, Tokyo (JP); Yasuhisa Shimakura, Tokyo (JP); Sadayuki Matsumoto, Tokyo (JP); Tateki Mitani, Tokyo (JP); Shigeki Kanamaru, Tokyo (JP); Kazushi Ishii, Tokyo (JP)

(73) Assignee: Mitsubishi Electric Corporation, Tokyo (JP)

( * ) Notice: Subject to any disclaimer, the term of this patent is extended or adjusted under 35 U.S.C. 154(b) by 84 days.

(21) Appl. No.: 11/914,271

(22) PCT Filed: May 22, 2006

(86) PCT No.: PCT/JP2006/310111

§ 371 (c)(1),
(2), (4) Date: Nov. 13, 2007

(87) PCT Pub. No.: WO2006/126468

PCT Pub. Date: Nov. 30, 2006

(65) Prior Publication Data

US 2009/0034901 A1 Feb. 5, 2009

(30) Foreign Application Priority Data

May 26, 2005 (JP) ............................. 2005-153939
Nov. 14, 2005 (JP) ............................. 2005-328622

(51) Int. Cl.
*G02B 6/00* (2006.01)
(52) U.S. Cl. ...................................................... 385/12
(58) Field of Classification Search .................... 385/12
See application file for complete search history.

(56) References Cited

FOREIGN PATENT DOCUMENTS

| JP | 1 282449 | 11/1989 |
|---|---|---|
| JP | 6 58878 | 3/1994 |
| JP | 10 26552 | 1/1998 |
| JP | 2000 9495 | 1/2000 |
| JP | 2000 221085 | 8/2000 |
| JP | 2003 194635 | 7/2003 |
| JP | 2004 294375 | 10/2004 |
| WO | 02 44697 | 6/2002 |

*Primary Examiner*—Jerry T Rahll
(74) *Attorney, Agent, or Firm*—Oblon, Spivak, McClelland, Maier & Neustadt, L.L.P.

(57) ABSTRACT

An optical fiber sensor that can detect a liquid level or detect a property of liquid with high reliability even under a frequently vibrational environment. The optical fiber sensor includes an optical fiber that includes a core having an area where a grating is formed and a clad, the optical fiber being disposed so that at least a part of the area with the grating is immersed in liquid, a light source for making light incident to the optical fiber so that a cladding mode light having a wavelength band is generated by the grating, and a light receiving unit for detecting the intensity of light which is incident from the light source to the optical fiber and transmitted through the grating.

20 Claims, 30 Drawing Sheets (a)

(b)

(a)

(b)

(b) AFTER CORRECTION (a) BEFORE CORRECTION (a)

(b)

(c)

OPTICAL FIBER SENSOR

TECHNICAL FIELD

The present invention relates to an optical sensor that can be used for a fuel gauge of a fuel tank in a vehicle or the like to detect liquid level or detect the property of liquid.

BACKGROUND ART

In a conventional liquid level detecting sensor for a fuel gauge, a bar joined to a float which is displaced in accordance with the height of the liquid level of fuel is rotated in accordance with the height of the liquid surface, and the height of the liquid level is detected on the basis of variation of a resistance value of a variable resistor provided to the movable shaft of the bar (for example, see Patent Document 1). The thus-constructed liquid level detecting sensor has a problem that the workability when the liquid level detecting sensor is secured to the fuel gauge insertion port is low because the bar joined to the float is larger than the diameter of the insertion port of the fuel gauge, and also a problem that metal powder may occur or such a trouble as short-circuit of a variable resistor may occur because there is some sliding portions in the fuel tank. In order to avoid these problems, a liquid level detecting sensor using an optical fiber is known. This liquid level detecting sensor is equipped with an optical fiber provided at a position where the height of the liquid level is desired to be detected, light emitting means for irradiating light a laser beam from one end portion of the optical fiber, and control means for determining a temperature distribution of the optical fiber on the basis of the intensity of back scattering light of the laser beam irradiated from the light emitting means and determining the height of the liquid level on the basis of the temperature distribution (see Patent Document 2, for example).

Furthermore, a sensor using an optical fiber for detecting the property of fuel is shown in Patent Document 3. The patent document 3 discloses a liquid property identifying sensor including a sensor probe with a tapered detector formed by subjecting an optical fiber to a fusing-drawing treatment over a predetermined length, a multiplexing optical coupler that is connected to the input terminal of the sensor probe and multiplexes light beams of at least two wavelengths so that the light beams of at least two wavelengths are incident to the input terminal, a demultiplexing optical coupler that is connected to the output terminal of the sensor probe and demultiplexes light of at least two wavelengths transmitted through the sensor probe, and light receiving means for detecting the amount of light of at least two wavelengths emitted from the output terminal of the demultiplexing optical coupler, the transmitted light amount of light incident from the input terminal being varied in accordance with the property of liquid in which the sensor probe is immersed.

[Patent Document 1]
JP-A-10-26552 (Page 5, FIG. 4)
[Patent Document 2]
JP-A-2004-294375 (Page 3, FIG. 1)
[Patent Document 3]
JP-A-6-58878 (Page 5, FIG. 1)

DISCLOSURE OF THE INVENTION

Problem to be Solved by the Invention

In the conventional liquid level detecting sensor using the optical fiber, the backscattered light of the laser beam is a Raman scattered light whose intensity is varied in accordance with the temperature, and it is based on the assumption that the temperature is different between a gas-phase portion and a liquid-phase portion. Accordingly, a temperature difference occurs in the optical fiber at the boundary (liquid level) between the gas-phase portion and the liquid-phase portion, and the liquid level is detected on the basis of the variation of the intensity of the backscattered light due to the temperature difference concerned. However, when the temperature difference between the gas-phase portion and the liquid-phase portion is small, the temperature distribution of the optical fiber is flat and thus the intensity variation of the backscattered light is also small. Therefore, there is a problem that it is difficult to detect the liquid level. Furthermore, when the liquid level varies up and down at all times due to vibration or the like although the temperature difference between the gas-phase portion and the liquid-phase portion is large, the temperature distribution of the optical fiber is moderate, and thus the intensity distribution of the backscattered light is also moderate. Therefore, there is also a problem that the detection error of the height of the liquid level is large.

When a sensor probe having a tapered detector which is formed by conducting the fusing-drawing treatment is used as a sensor for detecting the property of liquid, the diameter of a part of the sensor portion is smaller than that before the fusing-drawing treatment. Therefore, it is weak in mechanical strength and particularly there is a reliability problem when it is used under a frequently vibrational environment as in the case of a fuel tank.

The present invention has been implemented to solve the above problems, and has an object to provide an optical fiber sensor that can detect liquid level or the property of liquid with high reliability under even a frequently vibrational environment.

Means of Solving the Problem

An optical fiber sensor according to the present invention has an optical fiber that includes a core having an area with a grating formed thereon and a clad, the optical fiber being disposed so that at least a part of the area with the grating is immersed in liquid, a light source for making light to the optical fiber so that a cladding mode light having a wavelength band is generated by the grating, a photo detector for detecting the intensity of light which is incident from the light source into the optical fiber and transmitted through the area with the grating, and the optical fiber sensor is used to detect the liquid level of the liquid or detect the property of the liquid.

Effect Of The Invention

The optical fiber sensor detects the intensity of the light of the cladding mode transmitted through the area with the grating, the grating being dependent on the refractive index of liquid or gas around the area with granting, and thus the optical fiber sensor can detect the liquid level or detect the property of the liquid. The detection is performed on the basis of the difference in refractive index. Therefore, according to the optical fiber sensor, the liquid level can be detected even when the liquid level varies at all times due to vibration or the like and thus the temperature difference between the gas-phase portion and the liquid-phase portion is moderate. Furthermore, as compared with the method of forming a part of the optical fiber which is greatly narrowed by the fusing-drawing treatment or the like, the intensity of the optical fiber is larger, and it is hardly broken under even a frequently-vibrational environment, so that the liquid level or the property of liquid can be detected with high reliability.

BEST MODES FOR CARRYING OUT THE INVENTION

EMBODIMENT 1

Figure 1:
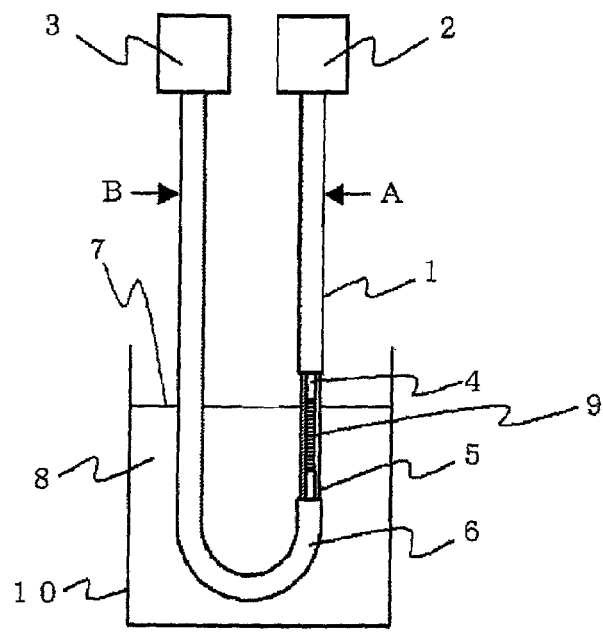
FIG. 1 is a schematic diagram showing an optical fiber sensor according to an embodiment 1 of the present invention.

FIG. 1 is a schematic diagram showing an optical fiber sensor for detecting the liquid level according to an embodiment 1 implementing the present invention. In FIG. 1, a light source 2 is disposed at one end portion of the optical fiber 1, and a light receiving unit 3 is disposed at the other end portion. The optical fiber 1 is equipped with a core 4 through which light emitted from the light source 2 propagates, a clad 5 covering the core 4 so that light is confined in the core 4, and a fiber jacket 6 which covers and protects the above elements. A part of the fiber jacket 6 is removed so that the clad 5 is brought into direct contact with liquid 8 to measure the height of the liquid level 7. The portion from which a part of the fiber jacket 6 is removed is disposed substantially in parallel to the variation direction of the liquid level 7, and a grating 9 is formed at the core 4 corresponding to this portion. The optical fiber 1 is bent in an U-shape in the neighborhood of the bottom surface of a container 10 in which the liquid 8 is stocked. The light source 2 and the light receiving unit 3 are disposed at the outside of the container 10.

A light emitting diode (LED), a laser diode (LD) or the like may be used as the light source 1, and a photo detecting element such as a spectral analyzer, a photodiode or the like may be used as the light receiving unit 3. Inorganic glass such as quartz glass or the like or a plastic type material such as polymethyl methacrylate or the like may be used for the core 4 and the clad 5. Resin such as fluorinated resin, nylon-based resin, phenol-based resin, epoxy-based resin, melanin-based resin or the like may be used for the fiber jacket 6.

As a method of forming the grating 9 in the core 4 may be used a method of disposing a phase mask at the portion from which the fiber jacket 6 is removed, and irradiating the phase mask with an excimer laser beam from the upper side of the phase mask to form a pattern of the grating corresponding to the relief of the phase mask to the core 4. The phase mask is achieved by forming plural grooves called as relief spaced at a fixed interval on the surface of a parallel flat plate formed of quartz glass, and the laser beam is periodically modulated by the relief. A photo-induced refractive index variation occurs in which the refractive index of a portion irradiated with the laser beam is higher than that of a non-irradiated portion occurs in the core 4, and thus the grating 9 in which the refractive index periodically varies is formed in the core 4. By changing the depth of the pitch or the depth of the grooves of the relief of the phase mask, the grating 9 having a desired pattern can be formed in the core 4. The grating is generally classified into a short-period grating having a refractive-index varying period of about 0.1 to 1 μm, and a long-period grating having a refractive-index varying period of about 100 to 1000 μm. The grating according to the present invention is limited to the former short-period grating, and all the gratings described in this specification means the short-period grating.

Next, the operation of this embodiment will be described. In general, a grating that can reflect only a certain signal to extract an optical signal having a certain specific wavelength propagating in an optical fiber transmission path is used in an optical communication system. A cladding mode described later exists in the transmission characteristic of the grating, and this cladding mode is of a problem because it is a loss ripple. The present invention rather utilizes the cladding mode which has been treated as an unnecessary thing in the optical communication system. The principle of measuring the liquid level utilizes the phenomenon that the intensity of light called as a cladding mode occurring when the light propagating in the core 4 is reflected from or transmitted through the grating 9 is varied in accordance with the refractive index of a material in contact with the outside of the clad 5. Light propagating in the core 4 is repetitively reflected at the boundary surface between the core 4 and the clad 5 and propagates through only the core 4 at the portion where no grating 9 is formed. However, when this light reaches the grating 9, the light is divided into light which transmits through the grating 9 and propagates in the core 4, light which suffers Bragg reflection in the grating 9 and propagates in the opposite direction in the core 4 and backward propagating cladding mode light which goes out from the core 4 to the clad 5 and propagates in the opposite direction in the clad 5. As described above, in the short-period grating used in the present invention, the cladding mode light propagates backward. However, the cladding mode light occurring in the long-period grating propagates forward.

Figure 2:
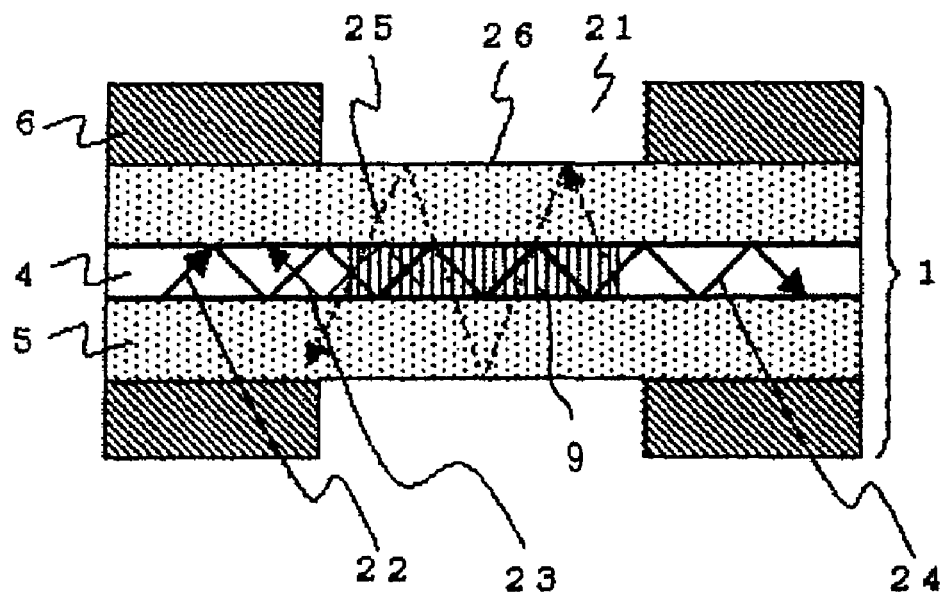
FIG. 2 is a diagram showing a cladding mode according to the embodiment 1 of the present invention.
Figure 2:
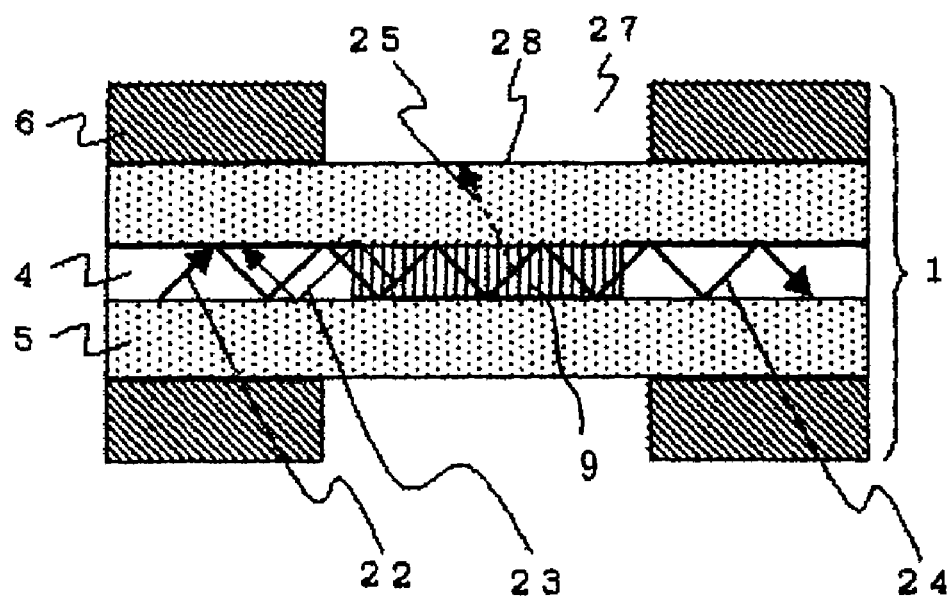

FIG. 2 is a diagram showing the relationship between the light of the cladding mode and the refractive index of the material in contact with the outside of the clad. The description will be made by exemplifying water as the liquid 8 and air as gas. FIG. 2(a) is a schematic diagram showing light propagation when the material in contact with the outside of the clad is air, and FIG. 2(b) is a schematic diagram showing light propagation when the material in contact with the outside of the clad is water. The refractive index of air is set to 1.0, the refractive index of water is set to 1.3, the refractive index of the core 4 is set to 1.36 and the refractive index of the clad 5 is set to 1.35. As shown in FIG. 2(a), when the outside of the clad 5 is air 21, propagating light 22 propagating from the light source is divided into reflection light 23 which is subjected to Bragg reflection by the grating 9, transmission light 24 transmitting through the grating 9 and propagating in the core 4 and cladding mode light 25 occurring by the grating 9. The cladding mode light 25 is reflected at the interface 26 between the clad 5 and the air 21 because the difference in refractive index between the clad 5 and the air 21 is large, that is, 0.35, and thus propagates in the clad 5. The light is confined in the clad and thus a loss ripple inherent to the cladding mode appears in the transmission characteristic. On the other hand, as shown in FIG. 2(b), when the outside of the clad 5 is water 27, the cladding mode light 25 occurring at the end portion of the grating 9 is little reflected at the interface 28 between the clad 5 and the water 27, and it transmits through the interface 28 and propagates to the water 24 because the difference in refractive index between the clad 5 and the water 27 is small, that is, 0.05, so that the light 25 propagates hardly in the clad 5. Therefore, the light is not confined in the clad, and thus no loss ripple appears in the transmission characteristic inherent to the cladding mode.

Figure 3:
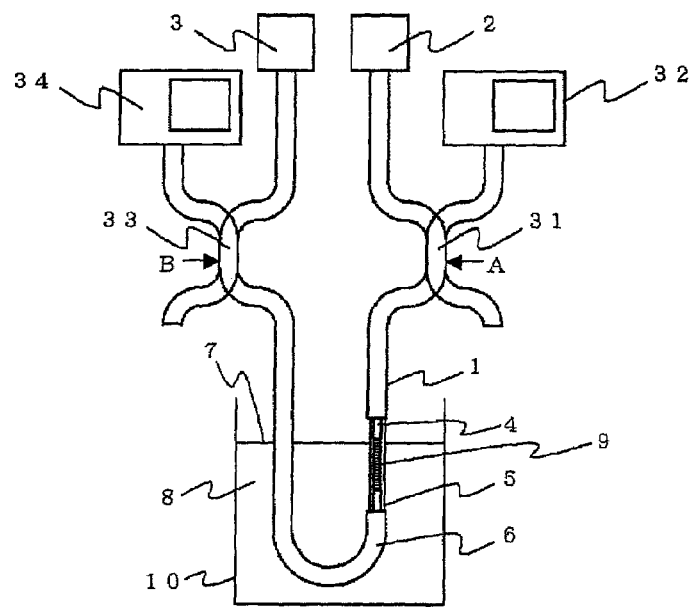
FIG. 3 is a diagram showing the connection between an optical coupler and a spectral analyzer according to the embodiment 1 of the present invention.
Figure 4:
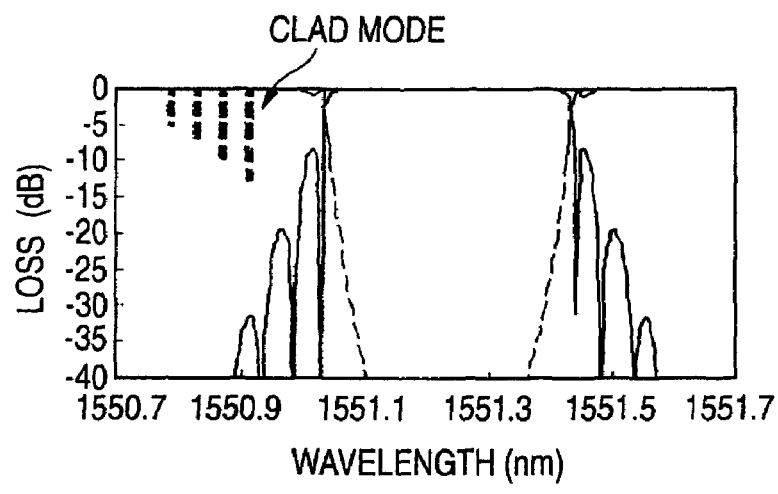
FIG. 4 is a diagram showing a transmission spectrum in the embodiment 1 of the present invention.
Figure 4:
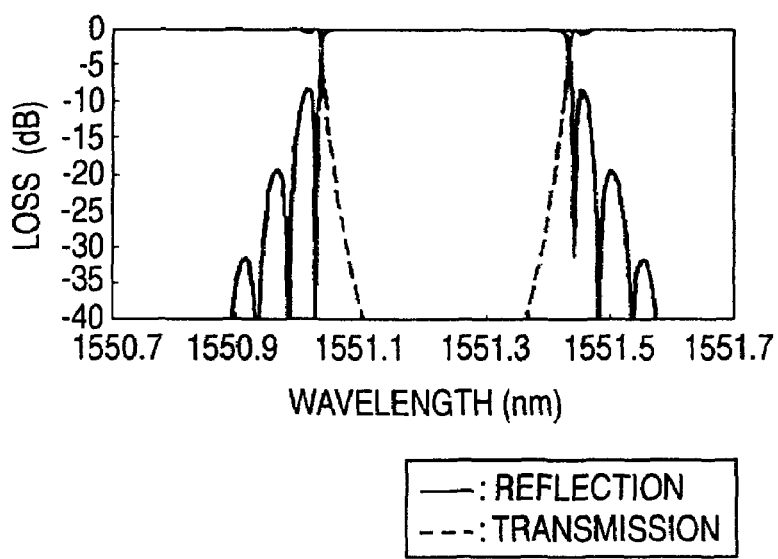

Furthermore, the operation of this embodiment will be described in detail. As shown in FIG. 3, an optical coupler 31 of 2×2 is connected to a point A between the light source 2 of the optical fiber 1 and the liquid level 7 as shown in FIG. 1, and the reflection spectrum of light reflected from the grating 9 is measured by a spectral analyzer 32. Furthermore, as shown in FIG. 3, an optical coupler 33 of 2×2 is connected to a point B between the liquid level 7 of the optical fiber 1 and the light receiving unit 3, and the transmission spectrum of light transmitted through the grating 9 is measured by a spectral analyzer 34. FIG. 4 shows the thus-measured reflection spectrum and transmission spectrum. FIG. 4(a) shows the reflection spectrum and the transmission spectrum when the material in contact with the outside of the clad is air, that is, when no water is stocked in the container 10, and FIG. 4(b) shows the reflection spectrum and the transmission spectrum when the material in contact with the outside of the clad is water, that is, when water is filled in the container 10. As is apparent from FIG. 4(a), when the material in contact with the outside of the clad is air, loss peaks of several to several tens which are caused by the cladding mode appear at a shorter wavelength side as compared with a wavelength area where a large loss appears at the center of the transmission spectrum. On the other hand, as is apparent from FIG. 4(b), when the material in contact with the outside of the clad is water, there appears no loss peak based on the cladding mode which appears in the transmission spectrum as shown in FIG. 4(a).

As described above, the presence or absence of the loss peak at the transmission spectrum which is caused by the cladding mode is dependent on the difference in refractive index of the material in contact with the outside of the clad, and thus the presence or absence of liquid can be detected. Furthermore, when a part of the grating is immersed in water, the peak height of the transmission spectrum which is caused by the cladding mode is varied in proportion to the length of the part immersed in water, and thus the height of the liquid level can be measured on the basis of the peak height.

Figure 5:
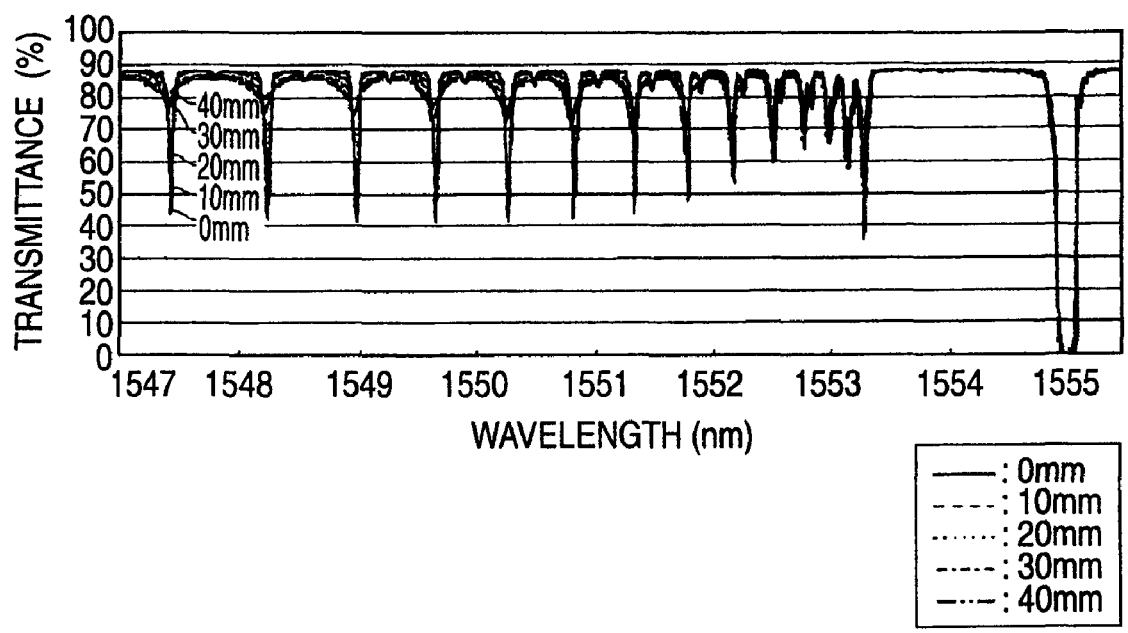
FIG. 5 is a characteristic diagram in the embodiment 1 of the present invention.

FIG. 5 shows the relationship between the height of the liquid level corresponding to the length of the immersed part of the grating 9 in liquid and the transmission spectrum of the transmitted light measured by the spectral analyzer when a broad band light source using spontaneous emission light of EDFA (Erbium Doped Fiber Amplifier) is used as the light source 2 and the spectral analyzer is used as the light receiving unit 3. Many valley-like peaks having low transmittance which appear in the area from 1547 to 1556 nm in wavelength are losses based on the cladding mode, and the depth of each peak is varied in accordance with the height of the liquid level.

Figure 6:
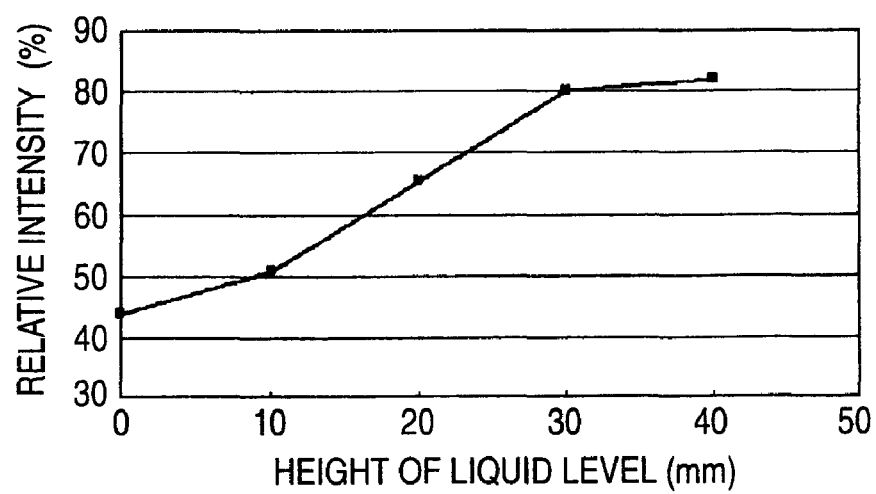
FIG. 6 is a characteristic diagram in the embodiment 1 of the present invention.

FIG. 6 is a characteristic diagram showing the relationship between the height of the liquid level and the relative intensity of light of 1547.4 nm in wavelength which corresponds to one of the loss peaks measured by the spectral analyzer of the light receiving unit 3. When the liquid level is high, the length of the grating immersed in water is increased, and occurrence of the cladding mode is suppressed. Therefore, the loss based on the cladding mode is reduced, and the light intensity at the light receiving unit is increased. When the liquid level is lowered, the loss based on the cladding mode is increased, and the light intensity at the light receiving unit is reduced. Accordingly, the height of the liquid level can be detected by measuring the depth of the loss peak of the transmission spectrum caused by the cladding mode.

When a photodiode is used as the light receiving unit, the height of the liquid level can be detected by measuring the relative intensity of transmitted light because the intensity of the transmitted light is lowered in accordance with the depth of the peak of the transmission spectrum based on the cladding mode.

In the thus-constructed liquid level detecting optical fiber, the intensity of the transmitted light varies in accordance with the difference in refractive index between air as a gas-phase portion and water as a liquid-phase portion, and on the basis of this, the liquid level is detected. Therefore, the liquid level can be detected even when the temperature difference between the gas-phase portion and the liquid-phase portion is small. Furthermore, even when the liquid level is varied due to vibration or the like at all times, the refractive index of the outside of the clad is limited to the refractive index of one of gas and liquid, and it is not equal to some intermediate value therebetween. Therefore, the height of the liquid level can be accurately detected. Accordingly, the grating-formed area may be disposed at any position insofar as the liquid level traverses the area concerned when the liquid level varies. The direction of the arrangement is not necessarily limited to the parallel direction to the variation direction of the liquid level, and it may be disposed obliquely or in parallel to the liquid level. For example, when the grating-formed area is disposed substantially in parallel to the liquid level at a position where the liquid level traverses the area concerned, it can be detected on the basis of the intensity of the transmitted light whether the liquid level is located at a higher position or lower position than the position concerned.

This embodiment has been described by exemplifying water of 1.35 in refractive index as liquid. However, when liquid is substance other than water, it is required to properly set the refractive index of the clad in conformity with the refractive index of liquid as a measurement target. At this time, in order to confine propagating light in the core, it is required to properly set the refractive index of the core at the same time. For example, the refractive index of gasoline is equal to about 1.4, the refractive indexes of liquefied propane and trichloroethane are equal to about 1.45. When an optical fiber sensor for detecting the liquid level of these liquid is used, it is required to select a clad having a refractive index which is substantially equal to the refractive index of these liquid.

Furthermore, in this embodiment, the grating called as a refractive index modulation type in which the refractive index varies periodically is used. However, a grating in which grooves are processed so as to be periodically arranged may be used.

EMBODIMENT 2

In the embodiment 1, light reaching the light receiving unit also contains light of a large-loss wavelength area which is not relevant to occurrence of the cladding mode and appears at the center of the transmission spectrum. For example, when a photodiode for measuring the intensity of light is used as the light receiving unit, a part of the light intensity to be measured is the light intensity irrelevant to the occurrence of the cladding mode, and thus the variation amount of the light intensity is relatively small due to the loss caused by the cladding mode, so that it would be impossible to enhance the measurement sensitivity. In the embodiment 2, the light of the wavelength area irrelevant to the occurrence of the cladding mode is excluded from the measurement.

Figure 7:
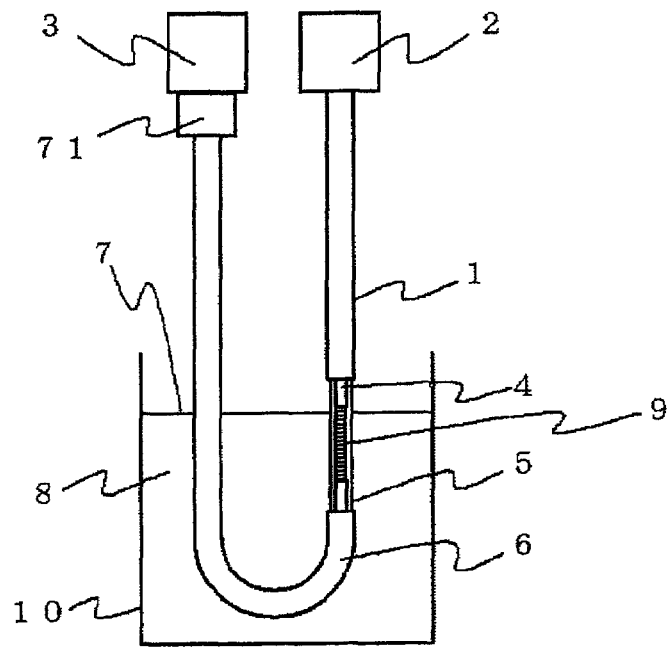
FIG. 7 is a schematic diagram showing an optical fiber of an embodiment 2 of the present invention.
Figure 8:
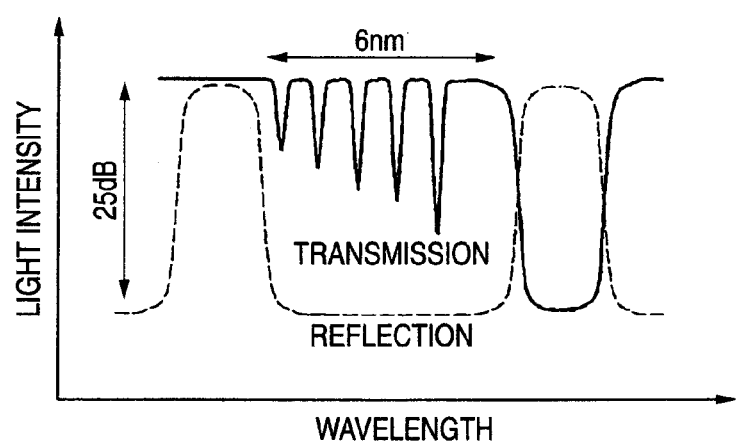
FIG. 8 is a characteristic diagram showing an optical fiber of the embodiment 2 of the present invention.

FIG. 7 is a schematic diagram showing a liquid level detecting sensor according to this embodiment. In this embodiment, in the same construction as the embodiment 1, an optical filter 71 is disposed at the portion where the optical fiber 1 is connected to the light receiving unit 3. A photodiode for measuring the light intensity is used as the light receiving unit 3. FIG. 8 is a characteristic diagram showing the relationship between the reflection spectrum of the optical filter 71 and the transmission light spectrum containing a loss caused by the cladding mode. As is apparent from FIG. 8, the optical filter 71 has a characteristic that it does not reflect the wavelength area containing a loss peak based on the cladding mode which appears in the spectrum of light, but reflects the other wavelength area. Therefore, the reflection characteristic is small, that is, 25 dB in the wavelength area containing the loss peak based on the cladding mode.

As described above, according to the construction that the light wavelength filter having a transmission area in the wavelength area of the cladding mode is provided, after light emitted from the light source 2 is transmitted through the grating 9, it propagates in the optical fiber 1 and reaches the light receiving unit 3. At this time, the optical filter 71 disposed in front of the light receiving unit 3 transmits therethrough only the light of the wavelength area containing the loss based on the cladding mode so that the light concerned reaches the light receiving unit 3, and reflects light of the other wavelength area. As a result, in the light receiving unit 3, the light intensity of only the wavelength area containing the loss peak based on the cladding mode is measured, so that the variation amount of the light intensity is greatly increased and the sensitivity of detecting the variation amount can be enhanced.

EMBODIMENT 3

In the embodiment 2, the light reflected from the optical filter may return to the light source or the grating to induce unnecessary interference, so that it becomes a noise component. In the embodiment 3, the light reflected from the optical filter is prevented from returning to the light source or the grating.

Figure 9:
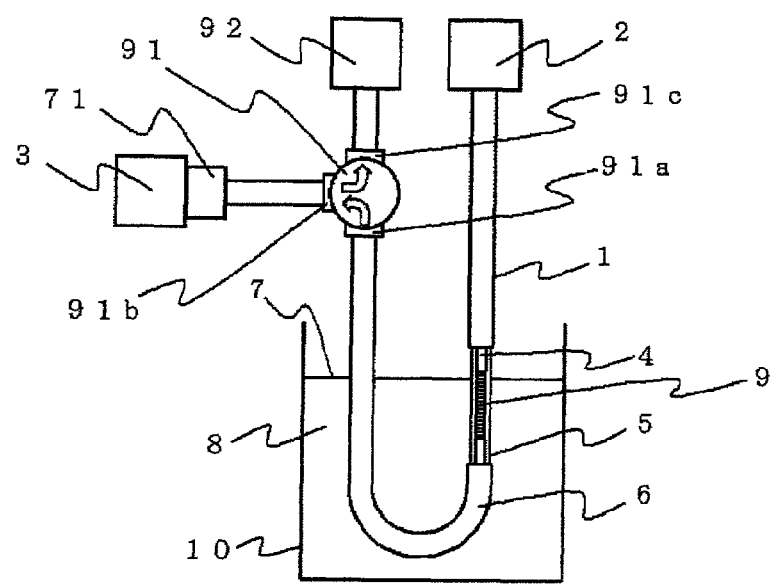
FIG. 9 is a schematic diagram showing an optical fiber of an embodiment 3 of the present invention.

FIG. 9 is a schematic diagram showing a liquid level detecting optical fiber sensor according to this embodiment. In this embodiment, in the same construction as the embodiment 2, a circulator 91 is disposed between the liquid level 7 and the optical filter 71, and the light reflected from the optical filter 71 is guided to a terminating unit 92 by the circulator 91. The circulator 91 has three ports 91a, 91b and 91c. The terminating unit 92 is a fiber coil of 10 mm or less in diameter. A photodiode for measuring the light intensity is used as the light receiving unit 3, for example.

The operation of this embodiment will be described. Light emitted from the light source 2 is transmitted through the grating 9, and propagates in the optical fiber 1. Then, the light is incident to the port 91a, and further emitted from the port 91b to the optical filter 71 side. In the optical filter 71, the light of the wavelength area containing the loss peak based on the cladding mode is transmitted and propagates to the light receiving unit 3 side. However, the light of the other wavelength area is reflected and returned to the port 91b. The light returned to the port 91b is emitted from the port 91c and reaches the terminating unit 92. The terminating unit 92 prevents reflection of incident light.

Figure 10:
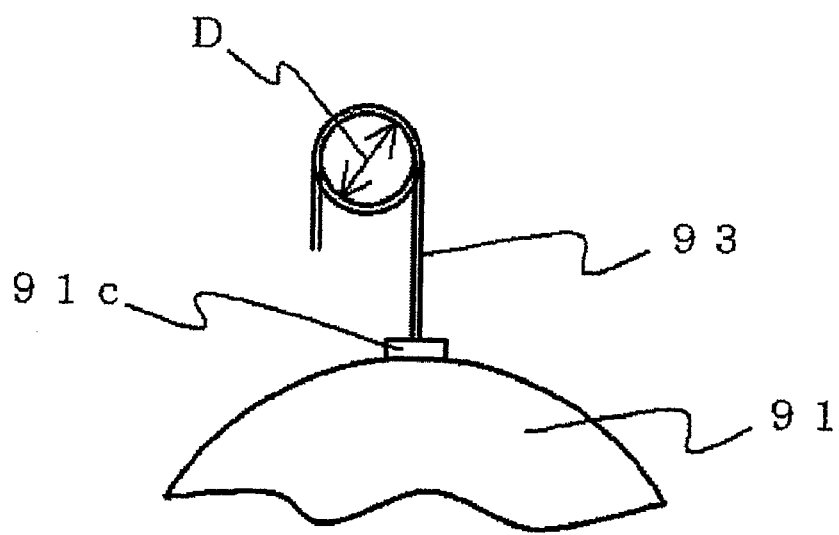
FIG. 10 is a schematic diagram showing a terminating unit of the embodiment 3 of the present invention.

FIG. 10 is a schematic diagram showing the terminating unit 92 of this embodiment. It is formed by winding the optical fiber 93 connected to the port 91c at many times with a diameter of D. By setting the diameter D to 10 mm or less, the bending loss of the optical fiber 93 is increased to prevent reflection.

According to the thus-constructed liquid level detecting sensor, by disposing the optical filter 71 at the incident side of the light receiving unit 3, the detecting sensitivity can be enhanced, and also it can be prevented that the light reflected from the optical filter 71 returns to the light source 2 or the grating 9 to induce unnecessary interference and thus becomes a noise component. Furthermore, by disposing the circulator 91 between the optical fiber 1 and the light receiving unit 3, the same effect can be also achieved in the construction that no optical filter 71 is provided in FIG. 9 because light which is a part of the light incident from the optical fiber 1 to the light receiving unit 3 and reflected from the surface of the light receiving unit 3 and incident to the optical fiber 1 again is prevented from returning to the light source 2 side.

In this embodiment, the fiber coil is used as the terminating unit, however, an antireflection film may be formed on the terminal of the optical fiber to prevent reflection.

EMBODIMENT 4

Figure 11:
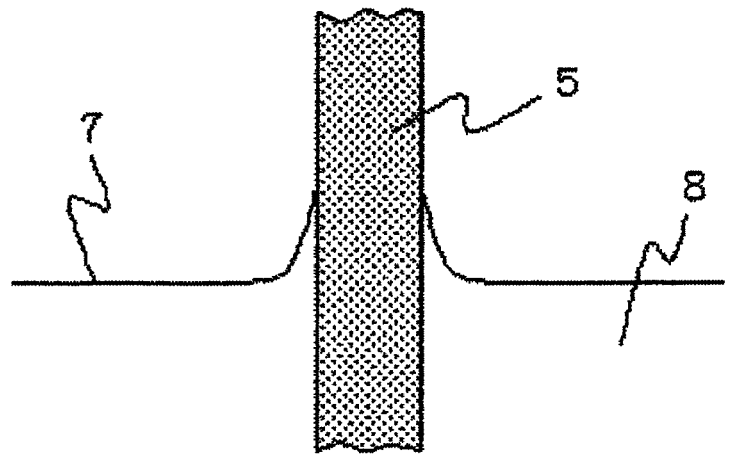
FIG. 11 is a diagram showing the interface between the clad and the liquid in an embodiment 4 of the present invention.

FIG. 11 is a diagram showing the state of the interface between the clad 5 of the optical fiber and the liquid 8. In FIG. 11, on the surface of the clad 5 which is in contact with the liquid 8, the liquid may rise up to a position higher than the liquid level 7 because of surface tension of the liquid 8 or wettability of the liquid 8 to the clad 5. The rising of the liquid as described above normally occurs by 1 to 2 mm, however, it rises up to a higher position when the wettability is more excellent. When such a phenomenon occurs, a position higher than the actual liquid level is measured as the liquid level. In the embodiment 4, the contact angle between the liquid and the clad is increased, and the height of the liquid level is accurately measured.

Figure 12:
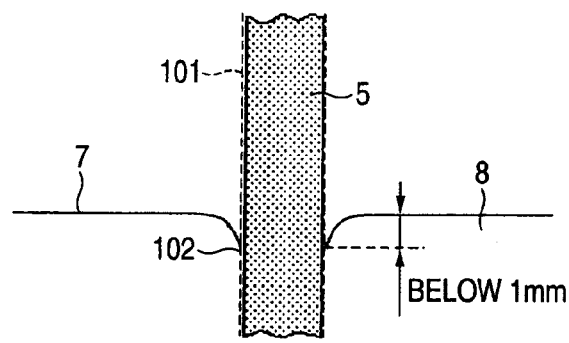
FIG. 12 is a diagram showing the interface between the clad and the liquid in the embodiment 4 of the present invention.

FIG. 12 is a diagram showing the interface state between the clad 5 and the liquid 8 in this embodiment. In FIG. 12, a water-shedding coating 101 which is water-shedding to the liquid 8 is formed on the surface of the clad 5 formed of quartz glass. The coating 101 is required to be selectively used in accordance with the type of the liquid 8 as a measurement target. For example, when the liquid is gasoline, the critical surface tension of gasoline is equal to about 30 $mJ/m^2$, and thus a material such as fluorinated resin having a critical surface tension of 6 to 20 $mJ/m^2$, graphite having a critical surface tension of about 45 $mJ/m^2$ or the like is suitable to the coating 101. If the film thickness of the coating 101 is so large, the difference in refractive index between the coating 101 and the clad 5 would be remarkable and thus the cladding mode would occur. Therefore, the film thickness of the coating 101 should not be so large. In order to increase the contact angle without inducing occurrence of the cladding mode, the film thickness of the coating 101 is preferably sets in the range from 50 to 1000 Å. The same liquid level detecting optical fiber sensor as the embodiment 1 is constructed by using the optical fiber having such a coating formed thereon.

In the thus-constructed liquid level detecting optical fiber sensor, the difference in height between the actual liquid level 7 and the contact line 102 of the clad 5 and the liquid 8 is equal to 1 mm or less as shown in FIG. 12, and thus the height of the liquid level can be more accurately measured as compared with the case where no coating is provided.

In this embodiment, the clad formed of quartz glass is used. However, the same effect can be achieved by using a clad formed of a plastic-based material such as polymethyl methacrylate or the like.

EMBODIMENT 5

In the embodiment 5, the material of the fiber jacket in the embodiments 1 to 4 is specified. Normally, the core and the clad of the optical fiber are formed of inorganic or organic glass material, however, the surface of the clad is liable to be scratched and the scratched portion is liable to expand even when they are in slight contact with each other. Therefore, a fiber jacket formed of organic material is formed around the clad for the purpose of protecting the clad. In this embodiment, the combination of the type of the liquid and the material of the fiber jacket is defined so that the fiber jacket is formed of a material which is chemical stable to the liquid. For example, when the liquid is gasoline, a material such as fluorinated resin-based, nylon-based, phenol-based, epoxy-based, and melanin-based material which are chemically stable to gasoline is used.

As constructed described above, the fiber jacket is not eluted into gasoline and the height of the liquid level can be stably measured. In addition, unnecessary materials are not contaminated into the liquid.

EMBODIMENT 6

Figure 13:
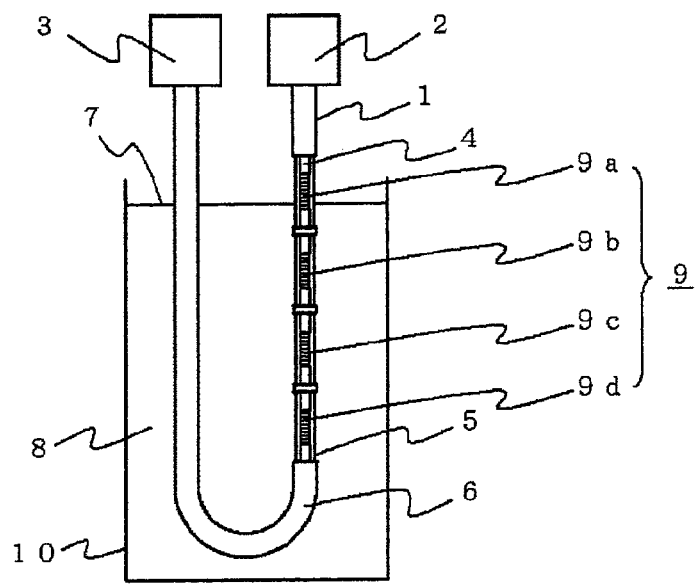
FIG. 13 is a schematic diagram showing an optical fiber sensor of an embodiment 6 of the present invention.

FIG. 13 is a schematic diagram showing a liquid level detecting optical fiber sensor according to an embodiment 6. In this embodiment, in the same construction as the embodiment 1, the grating 9 formed in the optical fiber 1 is divided into four areas. The grating 9 comprises divisional gratings 9a, 9b, 9c and 9d which are located to be nearer to the light source 2 in this order. An area in which no grating is formed is provided between the respective divisional gratings.

Next, the operation of the liquid level detecting optical fiber sensor according to this embodiment will be described. This embodiment is effective to detect the height of the liquid level at five stages. When the liquid level 7 is located to be lower than the divisional grating 9d nearest to the bottom surface of the container 10, cladding mode occurs in all the divisional gratings, and the intensity of the transmission light is minimum. Next, when the liquid level 7 rises up and the liquid 8 gradually immerses the divisional grating 9d, the intensity of the transmission light increases in accordance with the height of the liquid level 7. However, when the liquid level 7 reaches the non-grating formed area between the divisional gratings 9d and 9c, the intensity of the transmission light is set to a fixed value. When the liquid level 7 further rises up and reaches the divisional grating 9c, the intensity of the transmission light starts to rise up. As described above, the intensity of the transmission light varies stepwise when the liquid level 7 reaches each of the divisional grating areas.

As described above, a non-grating formed area exists between the respective divisional gratings exists, and thus the intensity of the transmission light varies stepwise every time when the liquid 8 immerses the divisional grating. Therefore, even when a photo detecting element having low resolving power is used as the light receiving unit 3, the height of the liquid level can be detected at five stages by detecting the stepwise variation of the intensity.

By constructing the divisional gratings so that the grating pitch is different among the divisional gratings, the wavelength of the loss peak based on the cladding mode occurring in each divisional grating is varied. Therefore, the height of the liquid level can be detected at five stages by detecting the loss peak wavelength at the light receiving unit by using a spectral analyzer.

EMBODIMENT 7

Figure 14:
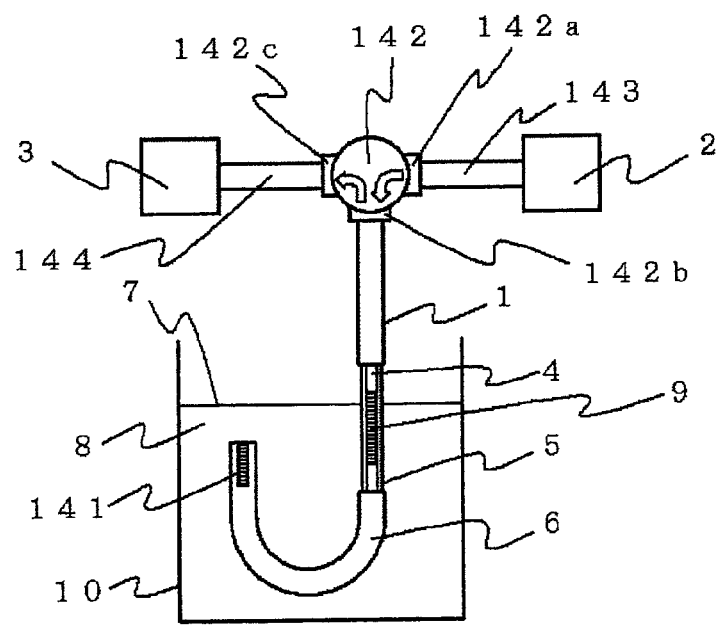
FIG. 14 is a schematic diagram showing an optical fiber sensor in an embodiment 7 of the present invention.

FIG. 14 is a schematic diagram showing a liquid level detecting optical fiber sensor according to an embodiment 7. In FIG. 14, a portion at which a part of the fiber jacket 6 of the optical fiber 1 is removed is disposed substantially in parallel to the variation direction of the liquid level 7, and a grating 9 is formed at the part of the core 4 which corresponds to this portion. A reflecting grating 141 for reflecting transmission light transmitted through the grating 9 is formed at one end portion of the optical fiber 1 immersed in the liquid 8. The reflecting grating 141 is formed in the optical fiber 1 at the opposite side to the light source 2 with respect to the area where the grating 9 is formed, and a wavelength band of Bragg reflection contains the wavelength of the light of the cladding mode, and the reflection grating 141 reflects the light of the wavelength band of the cladding mode transmitted through the area where the grating 9 is formed. The other end portion of the optical fiber 1 is connected to the port 142b of the circulator 142. The port 142a of the circulator 142 is connected to the light source 2 through the optical fiber 143, and the light receiving unit 3 is connected to the port 142c through the optical fiber 144.

Next, the operation of this embodiment will be described. Light emitted from the light source 2 is transmitted through the optical fiber 143 and incident to the port 142a, and then emitted from the port 142b to the optical fiber 1. Light propagating through the core 4 of the optical fiber 1 is divided to light transmitted through the grating 9 and propagating in the core 4, light subjected to Bragg reflection, and cladding mode light based on cladding mode. The cladding mode light varies in intensity in accordance with the length of the grating 9 immersed in the liquid 8, and as a result the intensity of the transmission light propagating in the core 4 varies. The transmission light transmitted through the grating 9 is reflected from the reflecting grating 141, and propagates to the circulator 142 side in the core 4. This reflected light varies in intensity in accordance with the length of the grating 9 immersed in the liquid 8 when it is transmitted through the grating 9 again. The light reaching the circulator 142 is transmitted from the port 142b to the port 142c, passed through the optical fiber 144 and then incident to the light receiving unit 3. The circulator 142 is provided to the end of the optical fiber 1 at the opposite side to the reflecting grating 141 with respect to the area where the grating 9 is formed, and it functions to make the light from the light source 2 incident from the end of the optical fiber 1 into the optical fiber 1 and also make the light receiving unit side receive the light emitted from the end of the optical fiber.

Figure 15:
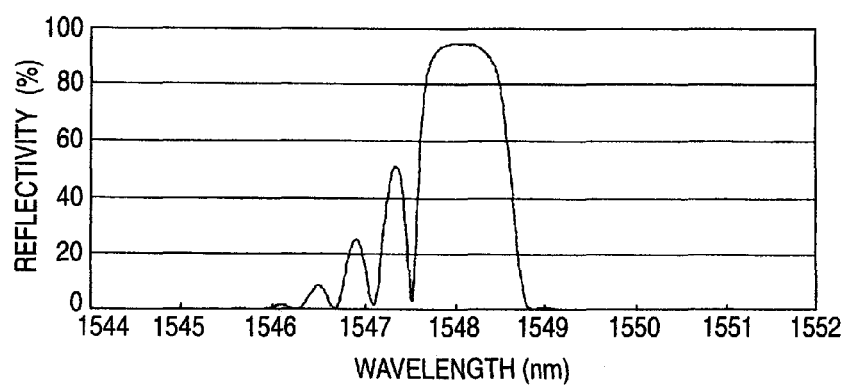
FIG. 15 is a characteristic diagram showing a reflection grating in the embodiment 7 of the present invention.
Figure 16:
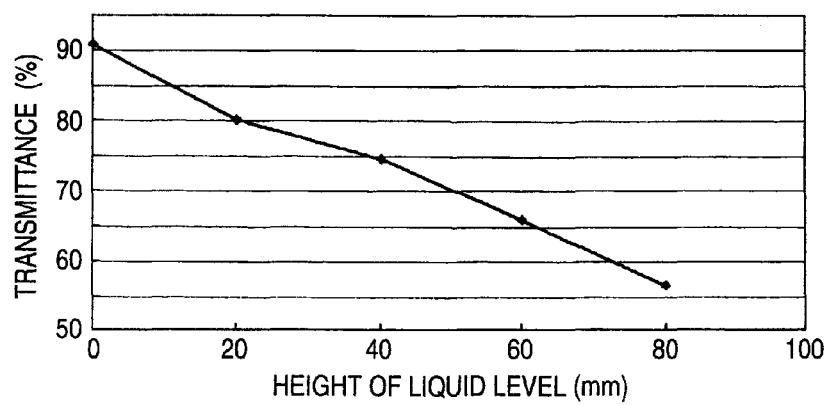
FIG. 16 is a characteristic diagram showing the reflection grating in the embodiment 7 of the present invention.

FIG. 15 shows a reflection spectrum of the reflecting grating 141 according to this embodiment. The reflecting grating 141 reflects light in the neighborhood of the wavelength of 1548.1 nm. FIG. 16 is a characteristic diagram when the intensity of light in the neighborhood of the wavelength of 1548.1 nm is measured with the light receiving unit 3 by using a broad band light source using spontaneous emission light of EDFA as the light source 2 and also using the spectral analyzer as the light receiving unit 3 as in the case of the embodiment 1 while the height of the liquid level 7 is changed. In this embodiment, by the variation of the area where the cladding mode exists, the loss based on the cladding mode increases as the height of the liquid level is higher, and the intensity of the transmission light transmitted through the grating is reduced. Accordingly, conversely to the embodiment 1, the intensity of light measured by the light receiving unit is lowered as the height of the liquid level rises as shown in FIG. 16.

In the thus-constructed optical fiber, light transmitted through the grating is reflected from the reflecting grating and transmits through the grating twice. Therefore, the variation of the light intensity is doubled and the measurement sensitivity is enhanced. Furthermore, it is unnecessary to fold back the optical fiber and thus the structure is simplified, so that the apparatus can be miniaturized.

EMBODIMENT 8

Figure 17:
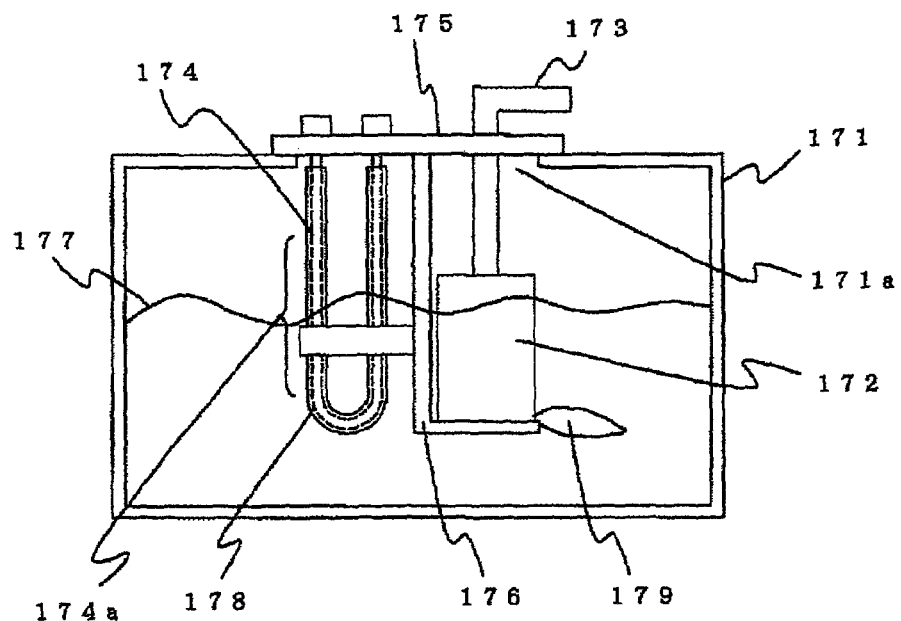
FIG. 17 is a schematic diagram showing a fuel gauge according to an embodiment 8 of the present invention.

FIG. 17 is a schematic diagram showing a fuel gauge using a liquid level detecting optical fiber sensor according to an embodiment 8. A plate 175 having a fuel pump 172, a discharge pipe 173 and an optical fiber sensor 174 is disposed at the opening portion 171a of an in-vehicle mount type fuel tank 171. The optical fiber sensor 174 is the same liquid level detecting optical fiber sensor as the embodiment 1, and it is fixed to the plate 175 by a support member 176 together with the fuel pump 172. The fuel gauge is constructed by the fuel pump 172, the discharge pipe 173 and the optical fiber sensor 174 fixed to the plate 175. A part of the optical fiber sensor 174 at which the grating 174a is formed is disposed substantially in parallel to the variation direction of the liquid level 177 of gasoline in the fuel tank 171. Furthermore, the optical fiber sensor 174 is covered by a perforated cover 178 for protection. When gasoline is supplemented, gasoline is supplied into the fuel tank through a fuel supply pipe (not shown) to the fuel tank 171.

Gasoline stocked in the fuel tank 171 is pumped up by the fuel pump 172 while the engine operates, and fed through the discharge pipe 173 to the engine. In order to prevent foreign matters such as dust, etc. in the fuel tank 171 from invading into the fuel pump 172, a low-pressure side filter 179 is secured to the suction port of the fuel pump 172. The liquid level 177 of gasoline shifts up and down in accordance with the supplement or use of gasoline. As described with reference to the embodiment 1, the height of the liquid level 177 can be detected by the grating 174a disposed substantially in parallel to the variation direction of the liquid level, so that the amount of gasoline in the fuel tank 171 can be measured.

In the thus-constructed fuel gauge, the up-and-down shift of the liquid level 177 of gasoline can be detected by the optical fiber sensor 174. Therefore, the liquid level can be detected even when the temperature difference between the gasoline 52 and the gas-phase portion (normally, air) of the fuel tank 171 is small, and also the height of the liquid level can be accurately detected even when the liquid level 177 of gasoline is varied due to vibration or the like at all times.

Furthermore, since the insertion cross-sectional area of the fuel gauge (the width and depth of the optical fiber sensor and the fuel pump) is small, the area of the opening portion 171a of the fuel tank can be reduced, and also the workability for fixing the fuel gauge can be enhanced.

Still furthermore, the optical fiber sensor is provided with no moving portion, and thus there does not occur any problem such as occurrence of dust due to aberration caused by sliding motion, etc.

EMBODIMENT 9

Figure 18:
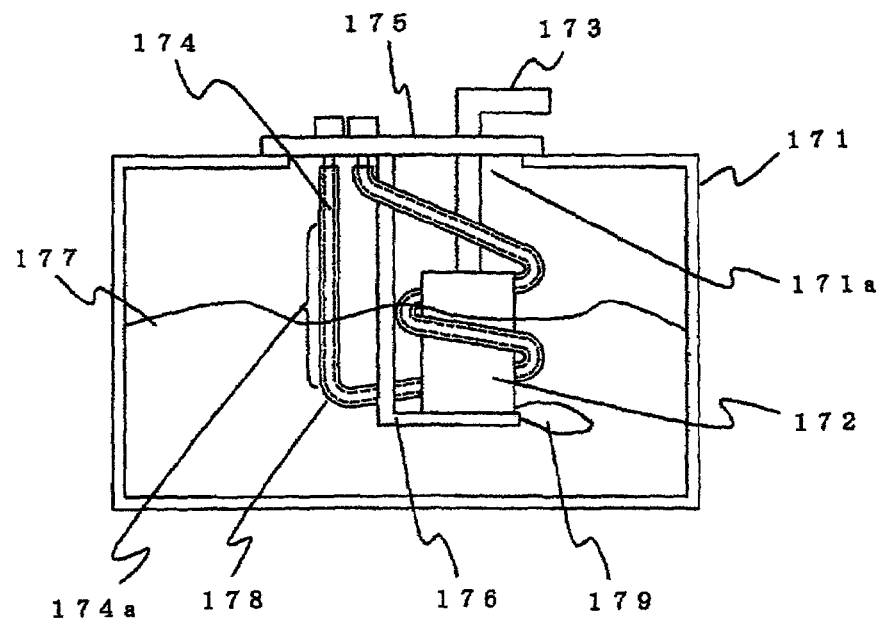
FIG. 18 is a schematic diagram showing a fuel gauge according to an embodiment 9 of the present invention.

FIG. 18 is a schematic diagram showing the fuel gauge using the liquid level detecting optical fiber sensor according to the embodiment 9. In this embodiment, the optical fiber at the portion of the optical fiber sensor 174 at which no grating is formed in the embodiment 8 is wound around the fuel pump 172. The portion of the optical fiber sensor 174 at which the grating 174a is formed is disposed substantially in parallel to the variation direction of the liquid level 177 of gasoline in the fuel tank 171.

According to the above construction, the fuel gauge can be further miniaturized.

EMBODIMENT 10

Figure 19:
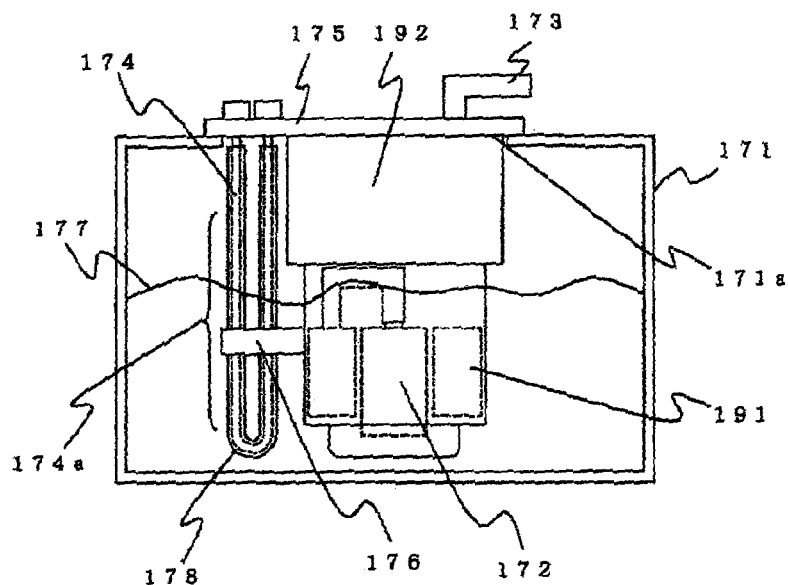
FIG. 19 is a schematic diagram showing a fuel gauge according to an embodiment 10 of the present invention.

FIG. 19 is a schematic diagram showing a fuel gauge using a liquid level detecting optical fiber sensor according to an embodiment 10. Gasoline pumped up by the fuel pump 172 is pressurized and fed to the discharge pipe 173. In this embodiment, a high-pressure side filter 191 is disposed at the outlet side of the fuel pump 172 to prevent foreign matters such as dust, etc. occurring in the fuel pump 172 from being fed to the discharge pipe 173. The fuel pump 172 and the high-pressure side filter 191 are accommodated in the fuel pump module 192. The optical fiber sensor 174 is fixed to the fuel pump module 192 by a support member 176. The portion of the optical fiber sensor 174 at which the grating 174a is formed is disposed substantially in parallel to the variation direction of the liquid level 177 of gasoline in the fuel tank 171.

In the thus-constructed fuel gauge, as in the case of the embodiment 8, the up-and-down shift of the liquid level 177 of gasoline can be detected by the optical fiber sensor 174. Therefore, the liquid level can be detected even when the temperature difference between gasoline and the gas-phase portion (normally, air) of the fuel tank 171 is small, and also the height of the liquid level can be accurately detected even when the liquid level 177 of gasoline varies due to vibration or the like at all times.

EMBODIMENT 11

Figure 20:
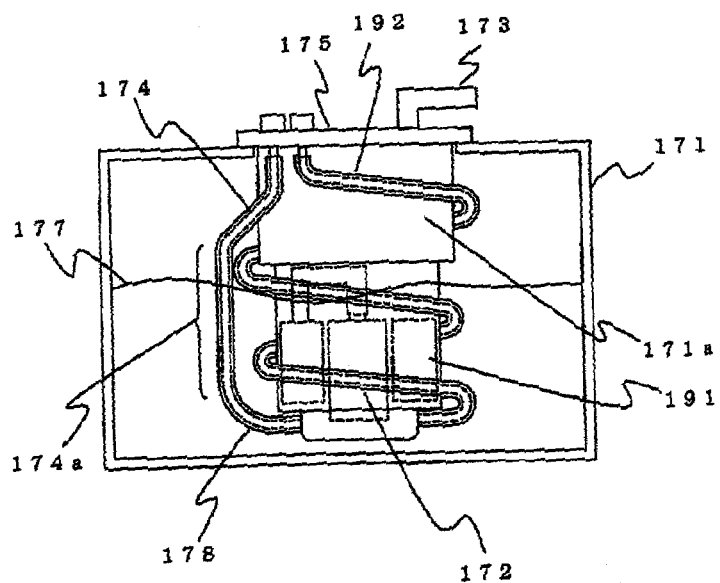
FIG. 20 is a schematic diagram showing a fuel gauge of an embodiment 11 of the present invention.

FIG. 20 is a schematic diagram showing a fuel gage using a liquid level detecting optical fiber sensor according to the embodiment 10. In this embodiment, the optical fiber of the portion of the optical fiber sensor 174 at which no grating is formed in the embodiment 10 is wound around the fuel pump module 192. The portion of the optical fiber sensor 174 at which the grating 174a is formed is disposed substantially in parallel to the variation direction of the liquid level 177 of gasoline in the fuel tank 171.

According to the above construction, the fuel gauge can be further miniaturized.

EMBODIMENT 12

Figure 21:
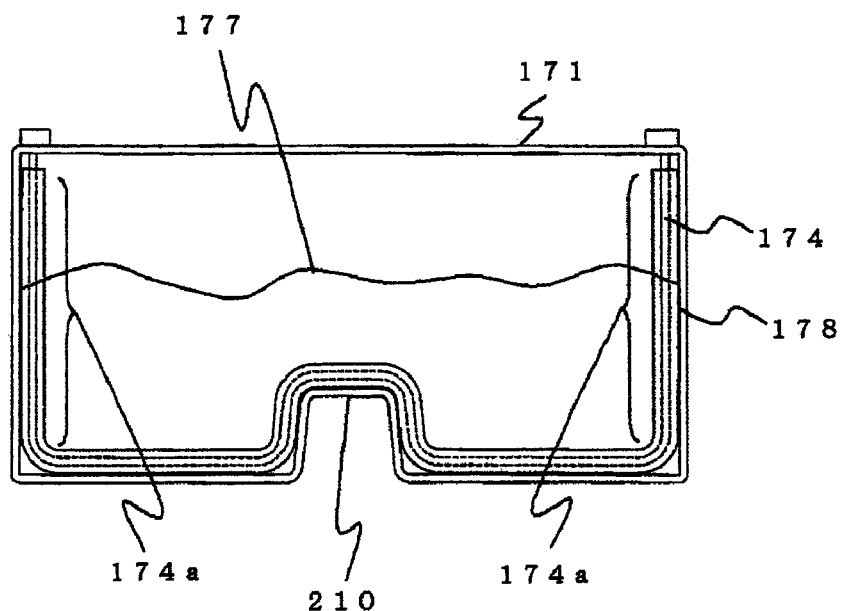
FIG. 21 is a schematic diagram showing an optical fiber sensor according to an embodiment 12 of the present invention.

FIG. 21 is a schematic diagram showing a fuel gauge using a liquid level detecting optical fiber sensor according to an embodiment 12. As one of fuel tanks for vehicles is known a tank having a saddle-shaped portion 210 in which a part of the bottom surface of the fuel tank projects inwardly. The fuel tank having such a complicated shape has a problem that it is difficult to dispose a conventional float type fuel gauge or it takes much labor to install the fuel gauge. In this embodiment, the optical fiber sensor 174 is disposed along the inner surface of the fuel tank 171 so as to stride over the saddle-shaped portion 210 from the inner side surface of the fuel tank 171, and the portion at which the grating 174a is formed is disposed substantially in parallel to the variation direction of the liquid level 177.

With the above construction, the fuel gauge can be mounted in a tank having a complicated shape or a compact tank.

EMBODIMENT 13

Light gasoline mainly containing hydrocarbon such as heptane, pentane, etc., heavy gasoline mainly containing hydrocarbon such as benzene, etc. and intermediate medium-gravity gasoline (normal regular gasoline) are known as pure gasoline used as fuel for vehicle engines. For example, when heavy gasoline is used as fuel for an engine which is set to control an ignition timing, etc. in conformity with light gasoline, the ignition timing is delayed. Therefore, not only degradation of starting performance at a low temperature and degradation of driving performance such as a breathing phenomenon or the like occurs, but also problems such as increase of harmful components in exhaust gas due to imperfect combustion, etc. occur. Fuel containing gasoline blended with alcohol to reduce the consumption amount of petroleum is growing popular to vehicles in respective countries such as U.S.A., Europe, etc. When such alcohol-blended fuel is directly applied to an engine which is matched with the air-fuel ratio of gasoline fuel, the air-fuel ratio is leaned because the theoretical air-fuel ratio of alcohol is smaller than gasoline or the like, and thus it is necessary to control an actuator such as a fuel injection valve or the like by detecting the rate of content of alcohol in the alcohol-blended fuel and adjust the air-fuel ratio, the ignition timing, etc. in accordance with the rate of content of alcohol. Accordingly, it is also necessary to detect "light", "heavy" of gasoline or the alcohol concentration, and further it is necessary to control the air-fuel ratio, the ignition timing, etc. in connection with the detection value.

Figure 22:
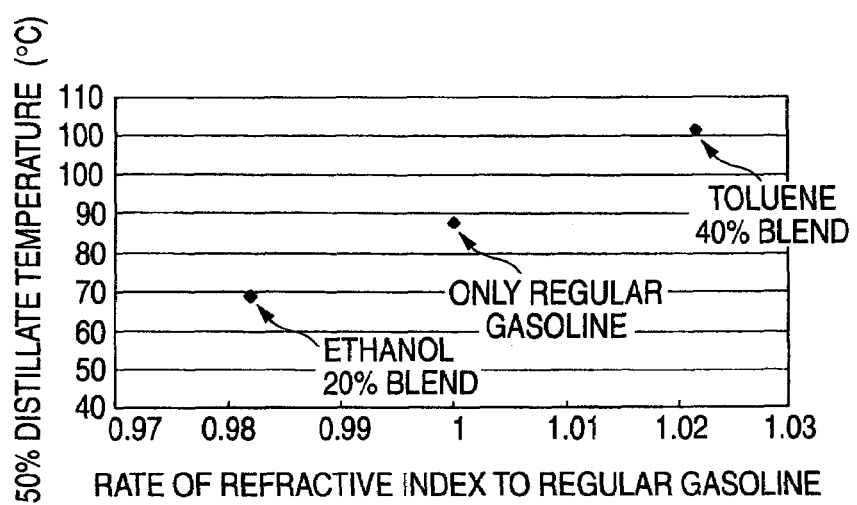
FIG. 22 is a graph showing a measurement result of the relationship between a refractive index ratio and distillation property of fuel.

FIG. 22 is a graph showing the relationship between the refractive index ratio to regular gasoline and 50%-distillation temperature as a distillation property in regular gasoline, gasoline containing regular gasoline blended with 20% ethanol and gasoline containing regular gasoline blended with 40% toluene. The distillation property was measured on the basis of "Distillation Test Method of Petroleum Product" of JIS K 2254. When Toluene is blended, the refractive index rate is large as indicated by a result, and the 50% distillation temperature is also large, so that the gasoline concerned becomes heavy gasoline. On the other hand, when ethanol is blended, the refractive index rate is small, and the 50% distillation temperature is also small, so that the gasoline concerned becomes light gasoline. As described above, "heavy" and "light" of gasoline are correlated to the refractive index of the gasoline, and the heavy gasoline has a large refractive index while the light gasoline has a small refractive index. Accordingly, by detecting the refractive index, the property of liquid can be detected.

Figure 23:
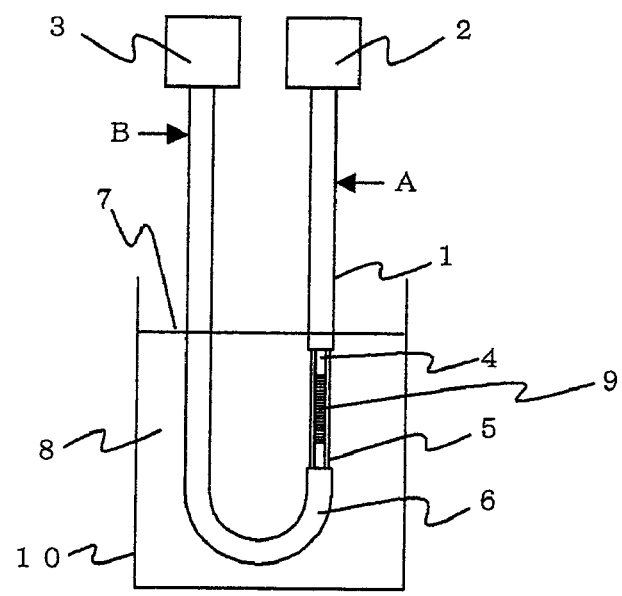
FIG. 23 is a schematic diagram showing the construction of an optical fiber according to an embodiment 13 of the present invention and a method of using the same.

FIG. 23 is a schematic diagram showing the construction of a liquid property detecting optical fiber sensor of the embodiment 13 and a method of using the same. The optical fiber sensor is equipped with a light source 2, a light receiving unit 3 and an optical fiber 1. The light source 2 is disposed at one end portion of the optical fiber 1, and the light receiving unit 3 is disposed at the other end portion. The optical fiber 1 is equipped with a core 4 in which light emitted from the light source 2 propagates, a clad 5 covering the core 4 to confine light in the core 4, and a fiber jacket 6 covering the clad 5 and the core 4 to protect them. A part of the fiber jacket 6 is removed so that the clad 5 comes into direct contact with liquid 8 to detect the property of the liquid. A grating 9 is formed in the core 4 corresponding to the portion at which a part of the fiber jacket 6 is removed.

The optical fiber sensor is used so that the portion of the optical fiber 1 at which a part of the fiber jacket 6 is removed and the grating 9 is formed is immersed in the liquid 8 stocked in the container 10, for example, as shown in FIG. 23. The optical fiber 1 is bent in a U-shape in the neighborhood of the bottom surface of the container 10 in which the liquid 8 is stocked, and the light source 2 and the light receiving unit 3 are disposes at the outside of the container 10. In order to measure the property of the liquid 8 irrespective of the amount of the liquid 8 in the container 10, it is desired that the grating is disposed so as to be as near to the bottom surface of the container 10 as possible. For example, the grating 9 may be disposed along the bottom surface.

With respect to the portion at which a part of the fiber jacket 6 is removed, it can be detected from any direction with respect to the liquid level insofar as it is immersed in the liquid 8.

Furthermore, the cladding mode occurs hardly at a portion at which the fiber jacket 6 is removed, but no grating is formed, and thus the portion concerned is hardly affected by the refractive index of the surrounding.

For example, LED, LD or the like may be used as the light source 2, and a light receiving element such as a photodiode or the like may be used as the light receiving unit 3. Inorganic glass such as quartz glass or the like, or plastic-type material such as polymethyl methacrylate or the like may be used for the core 4 and the clad 5, and resin of fluorinated type, nylon type, phenol type, epoxy type, melanin type or the like may be used for the fiber jacket 6.

Light incident from the light source 2 to the optical fiber 1 propagates in the core of the optical fiber, and reaches the grating 9. In accordance with the wavelength of the light, the light reaching the grating 9 is divided to light which is transmitted through the grating 9 and propagates in the core, light which suffers Bragg reflection with the grating 9 and thus propagates in the opposite direction in the core, and cladding mode light which goes out from the core to the clad and propagates in the clad. The light receiving unit 3 is provided at the destination to which the light of the optical fiber 1 propagates, and thus the intensity of the light transmitted through the grating 9 and propagating in the core and the intensity of the cladding mode light going out from the core to the clad and propagating in the clad can be detected.

Particularly, by a method of inserting an optical filter or the like, the wavelength band of light incident from the light source 2 to the optical fiber 1 or the wavelength band of light received before the light receiving unit 3 is limited to only the wavelength band in which the cladding mode light propagates, whereby the transmission light intensity of only the cladding mode light going out from the core to the clad and propagating in the clad can be detected.

The wavelength characteristic of the transmission light intensity of the cladding mode at the grating-formed portion has the transmission characteristic having loss peaks periodically as described above. The loss peaks are varied in magnitude in accordance with the difference in refractive index between the clad and the medium at the outside of the clad.

In the embodiment 1, the transmission light intensity of the cladding mode is greatly varied on the basis of the large difference in refractivity between liquid and gas. However, even when slightly different liquid is used as the medium at the outside, the intensity of the transmission light of the cladding mode is varied. In FIG. 23, the whole of the area where the grating 9 is formed is immersed in liquid, and thus the transmission light intensity of the grating portion corresponds to the refractive index of the liquid.

Figure 24:
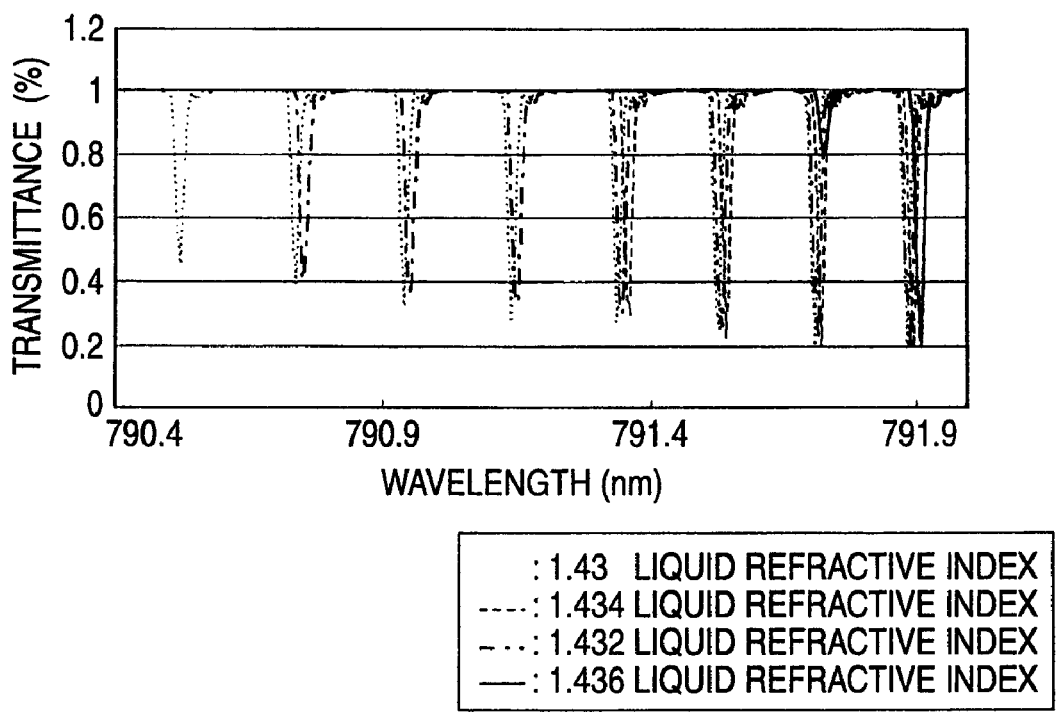
FIG. 24 is a graph showing a wavelength characteristic of transmittance of a grating according to the embodiment 13 of the present invention.

FIG. 24 is a graph showing the wavelength characteristic of the transmittance of the grating when the refractive index of liquid is varied. As the grating is used a grating having a core refractive index of 1.459, a clad refractive index of 1.444, a grating length of 10 mm, a grating period of 274 nm and a Bragg reflection wavelength in the neighborhood of about 796 nm. A broad band light source covering the wavelength area of the graph is used as the light source to measure the wavelength characteristic of the transmittance of the grating, and a spectral analyzer is used as the light receiving unit. The transmittance is calculated by setting as a reference value of 1.0 the transmission light intensity under the condition that the transmission light intensity is maximum, that is, under the state that the grating portion is immersed in liquid having a larger refractive index than the refractive index of the clad. As shown in FIG. 24, there is a tendency that the loss peak of the cladding mode is gradually reduced from the lower wavelength side as the refractive index of the liquid is gradually increased from 1.43 to 1.436 and finally the loss peak vanishes. Furthermore, when the refractive index of the liquid at the outside of the clad is equal to or higher than that of the clad, the cladding mode is radiated and thus it does not exist, so that all the loss peaks based on the cladding mode vanish. The intensity of the transmission light having the wavelength band of the cladding mode and transmitting through the grating is measured with the construction shown in FIG. 23 by using the above phenomena, whereby the refractive index of the liquid, that is, the property of the liquid can be detected.

Figure 25:
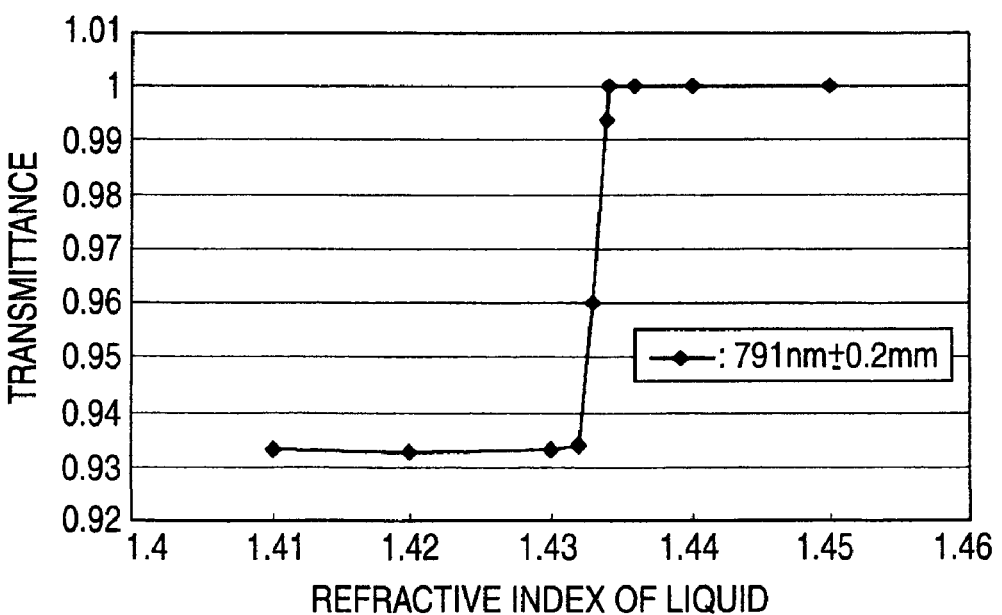
FIG. 25 is a graph showing the dependency of the transmittance of the grating to the refractive index of liquid in the embodiment 13 of the present invention.

FIG. 25 is a graph showing the dependency of the transmittance of the grating to the refractive index of the liquid when the wavelength of light input to the optical fiber 1 is equal to 791±0.2 nm. The wavelength band of 791±0.2 nm is a wavelength band containing a loss peak of a third cladding mode from the left side on the graph of FIG. 24. When the wavelength band of the light source 1 is broad, an optical filter through which only the wavelength band of 791±0.2 nm is transmitted may be disposed at the front stage of the light receiving unit or the like to achieve the same result.

As shown in FIG. 25, with respect to the transmission light intensity of the grating when the refractive index of liquid is varied, the transmittance is fixed to 0.933 when the refractive index of the liquid is equal to 1.43 or less, however, the transmittance rapidly increases when the refractive index of the liquid is in the range from 1.432 to 1.434. When the refractive index is equal to 1.434 or more, the transmittance is fixed to about 1.0. The wavelength-dependent characteristic of the transmittance corresponds to the variation in magnitude of the loss peak of the third cladding mode from the left side on the graph of FIG. 24.

When the light source 2 or the light receiving unit 3 is set so that the wavelength band containing the loss peak of a certain cladding mode is detected, the transmission light intensity varies stepwise with a specific refractive index as the boundary. Accordingly, by identifying whether the refractive index of the liquid is larger or smaller than a certain refractive index, the property of liquid, for example gasoline as to whether gasoline is light or heavy can be identified.

In this case, first, LD having the following wavelength is used as the light source 2 so that the transmittance of the wavelength band containing a loss peak of a proper one cladding mode whose intensity varies greatly at the boundary set to the refractive index of liquid whose property should be detected, for example, 1.433 in FIG. 25, or an optical filter for transmitting only the light of the wavelength concerned is disposed in front of the light receiving unit 3. Furthermore, the light receiving unit 3 is equipped to a circuit for emitting a signal at the time point when the transmission light intensity detected by the light receiving unit 3 exceeds a proper threshold value, for example, the transmission light intensity corresponding to the refractive index of 0.96 in the case of FIG. 25. Therefore, when the refractive index of the immersing liquid is larger than a specific refractive index, a signal is output from the light receiving unit 3 and thus the property of the liquid can be easily detected.

Figure 26:
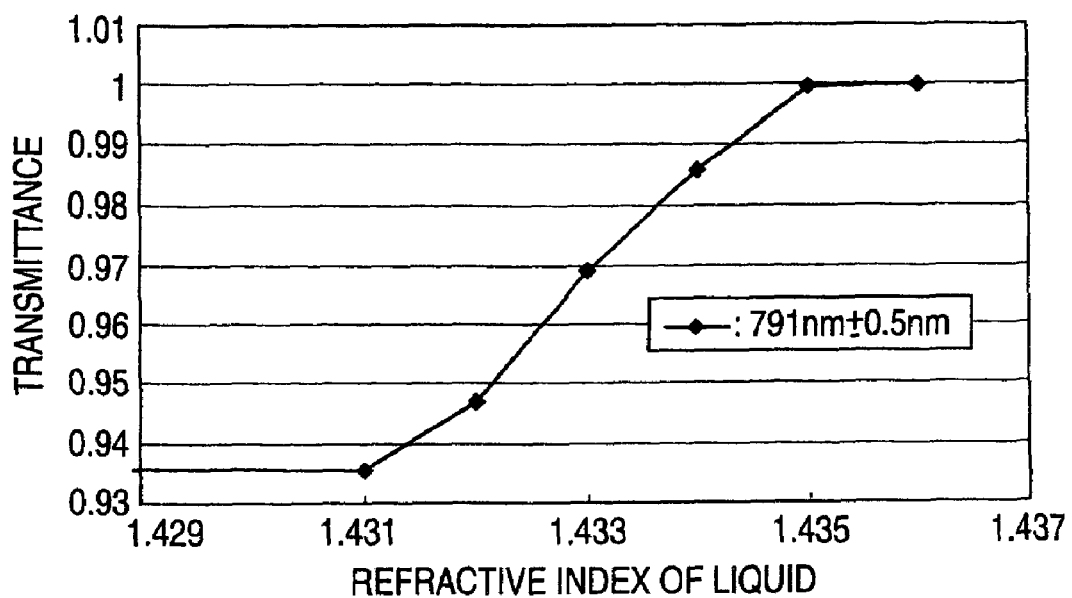
FIG. 26 is a graph showing the dependency of the transmittance of the grating to the refractive index of liquid in the embodiment 13 of the present invention.

FIG. 26 is a graph showing the dependency of the transmittance of the grating to the refractive index of the liquid when the wavelength band of light input to the optical fiber is 791±0.5 nm. The wavelength band of 791±0.5 nm is a wavelength band containing loss peaks of first to fifth cladding modes from the left side on the graph of FIG. 24. When the wavelength band of the light source 1 is board, a filter for transmitting only the wavelength band of 791±0.5 nm may be disposed in front of the light receiving unit.

In the above case, the transmission light intensity of the whole wavelength area containing the loss peaks of the cladding mode which are successively generated or vanish as the refractive index is varied from the first liquid at the left side to the fifth liquid on the graph of FIG. 24 is detected by light receiving unit. Accordingly, as shown in FIG. 26, with the transmission light intensity of the grating when the refractive index of liquid is varied, the transmittance is fixed to 0.936 when the refractive index of liquid is equal to 1.431 or less, however, the transmittance linearly increases with respect to the refractive index of liquid when the refractive index of liquid is in the range from 1.431 to 1.435. When the refractive index is equal to 1.435 or more, the transmittance is fixed to about 1.0.

When the wavelength band of the light source 2 or light receiving unit 3 so as to detect the transmittance of a wavelength band containing loss peaks of plural cladding modes, it is apparent that the variation of the transmittance with respect to the refractive index of liquid is linear. As compared with the case of FIG. 25 in which the transmittance is detected in the wavelength containing a loss peak of one cladding mode, the magnitude of the refractive index can be continuously measured for liquid in a broad refractive index range.

In this case, the wavelength band containing loss peaks based on plural cladding modes are selected so that the transmittance is linearly varied in the range of the refractive index of liquid whose property is required to be detected, for example, in the range from 1.431 to 1.435 in FIG. 26, LD of the wavelength concerned is used as the light source 2 or an optical filter for transmitting only the light of the wavelength concerned is disposed in front of the light receiving unit 3, and the transmission light intensity of the cladding mode is detected by the light receiving unit 3. When the refractive index of liquid in which the grating-formed area is immersed is in the above refractive-index range, the transmission light intensity corresponding to the transmittance of 0.936 to 1.0 is detected in accordance with the refractive index by the light receiving unit 3, so that the refractive index or the property of the liquid can be detected. If there is provided a circuit or the like for converting an output signal representing the transmission light intensity detected by the light receiving unit 3 to a signal representing the refractive index or the property of the liquid, the detection can be more easily performed.

Figure 27:
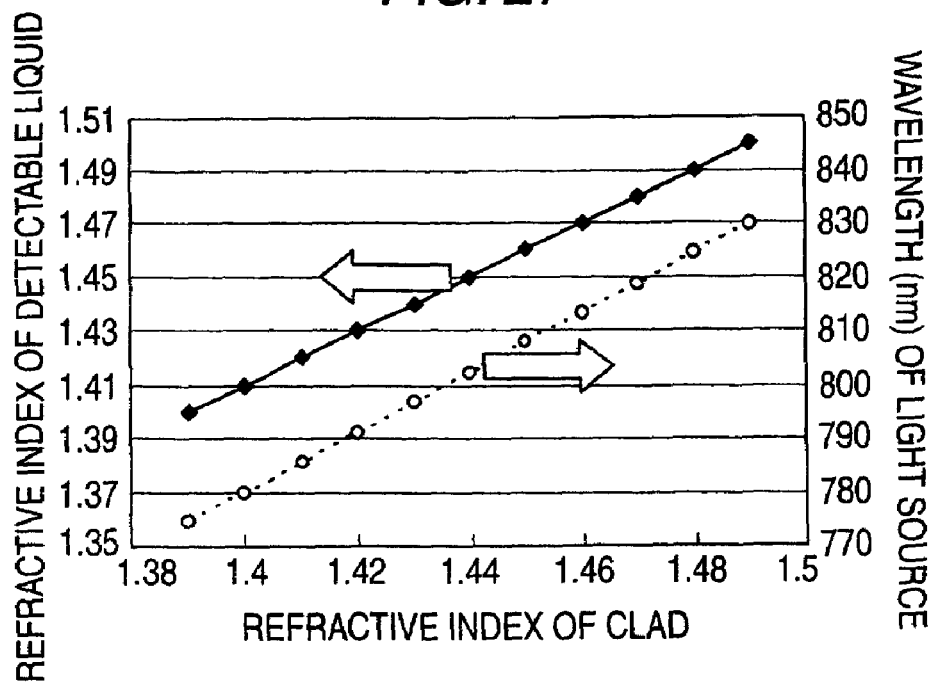
FIG. 27 is a graph showing the combination of the refractive index of liquid and the wavelength of a light source in the embodiment 13 of the present invention.

In the above case, the core refractive index is set to 1.459 and the clad refractive index is set to 1.444. However, by changing these refractive indexes, the measurable refractive index of liquid can be adjusted, and thus various kinds of liquid can be detected. FIG. 27 is a graph showing an example of the combination between the detectable liquid refractive index and the wavelength of the light source used at that time. The refractive index of the core is determined under the condition that the refractive index difference is set to 1%. As shown in the graph of FIG. 27, the refractive index of the clad increases and the detectable liquid refractive index increases. At this time, the wavelength spectrum shifts to a higher wavelength side as a whole, and thus the wavelength of the light source is also lengthened in connection with the shift of the wavelength spectrum as shown in the graph of FIG. 27. The refractive index of gasoline group is equal to 1.4 for small one and about 1.46 for large one, and by adjusting the refractive index of the clad, "heavy" or "light" of gasoline and the concentration of alcohol can be detected. In other combinations than that shown in the graph of FIG. 27, the detectable liquid refractive index can be changed by changing the period of the grating or the like.

As described above, the optical fiber sensor is set so that the whole area where the grating is formed is immersed in liquid, and thus the property of the liquid can be detected by detecting the light intensity of the cladding mode passing through the grating-formed area with the light receiving unit. Furthermore, the optical fiber has no part which is greatly narrowed in size through the fusing-drawing treatment or the like, and thus the intensity is large and the optical fiber sensor is hardly broken by stress based on vibration.

In this case, the grating adaptive to the wavelength around the 800 nm band is used, however, a grating adaptive to the 1500 nm band as in the case of the embodiment 1 or other wavelength bands may be used.

EMBODIMENT 14

Figure 28:
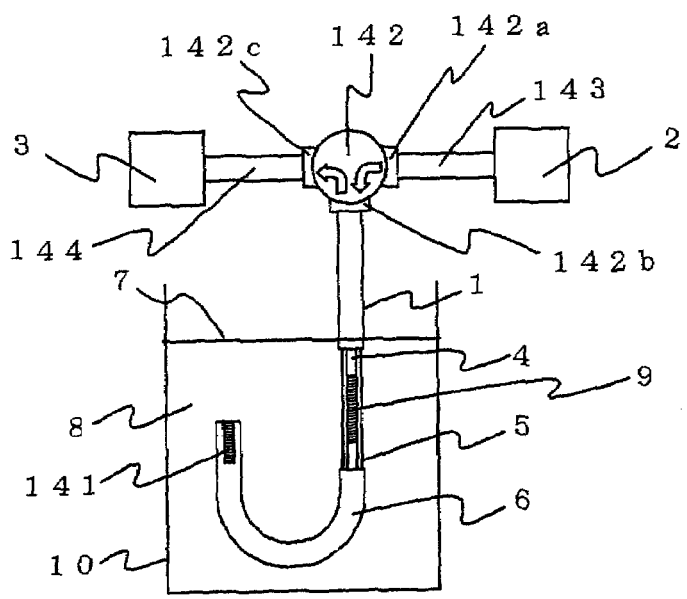
FIG. 28 is a schematic diagram showing the construction of an optical fiber according to an embodiment 14 of the present invention and a method of using the same.

In the embodiment 13, the grating is constructed as a transmission type in which light is transmitted only once. However, it may be constructed as a reflection type in which reflecting means is provided to the optical fiber 1 at the opposite side to the light source 2 with respect to the grating-formed area and light incident from the light source is returned from the reflecting means. FIG. 28 is a schematic diagram showing the construction of an optical fiber sensor for detecting a liquid property according to an embodiment 14, and a method of using the same. In FIG. 28, the whole portion of the optical fiber 1 at which a part of the fiber jacket 6 is removed is immersed in the liquid 8, and the grating 9 is formed at the core 4 corresponding to the portion concerned. A reflecting grating 141 for reflecting transmission light transmitted through the grating 9 is formed at one end portion of the optical fiber 1 which is immersed in the liquid 8. The reflecting grating 141 is provided to the optical fiber 1 at the opposite side to the light source 2 with respect to the area in which the grating 9 is formed, and the wavelength band of Bragg reflection of the reflecting grating 141 contains the wavelength of the light of the cladding mode. The reflecting grating 141 reflects the light of the wavelength band of the cladding mode transmitted through the area in which the grating 9 is formed. The other end portion of the optical fiber 1 is connected to the port 142b of the circulator 142. The light source 2 is connected through the optical fiber 143 to the port 142a of the circulator 142, and the light receiving unit 3 is connected through the optical fiber 144 to the port 142c.

Next, the operation will be described. Light emitted from the light source 2 is passed through the optical fiber 143, incident to the port 142a and emitted from the port 142b to the optical fiber 1. Light propagating through the core 4 of the optical fiber 1 is divided to light which is transmitted through the grating 9 and propagates in the core 4, light which is subjected to Bragg reflection, and light of cladding mode. The intensity of the cladding-mode light varies in accordance with the refractive index of the liquid 8 in which the grating 9 is immersed, so that the intensity of the transmission light propagating in the core 4 varies. The transmission light transmitted through the grating 9 is reflected from the reflecting grating 141, and propagates to the circulator 142 side in the core 4. When this reflected light is transmitted through the grating 9 again, the intensity thereof varies in accordance with the refractive index of the liquid 8 in which the grating 9 is immersed. Light reaching the circulator 142 is transmitted from the port 142b to the port 142c, passed through the optical fiber 144 and then incident to the light receiving unit 3 to detect the intensity thereof. Accordingly, if the relationship between the refractive index of the liquid 8 and the intensity of light incident to the light receiving unit 3 is investigated in advance, the refractive index of the liquid 8 can be detected from the intensity of light incident to the light receiving unit 3.

In place of the reflecting grating 141, the reflecting means may be formed by depositing metal to the terminal of the optical fiber.

When the reflecting grating 141 is used as the reflecting means, it is not necessarily disposed at the terminal of the optical fiber, and the reflecting grating 141 may be formed at any place of the optical fiber at the opposite side to the light source with respect to the grating-formed area.

Figure 29:
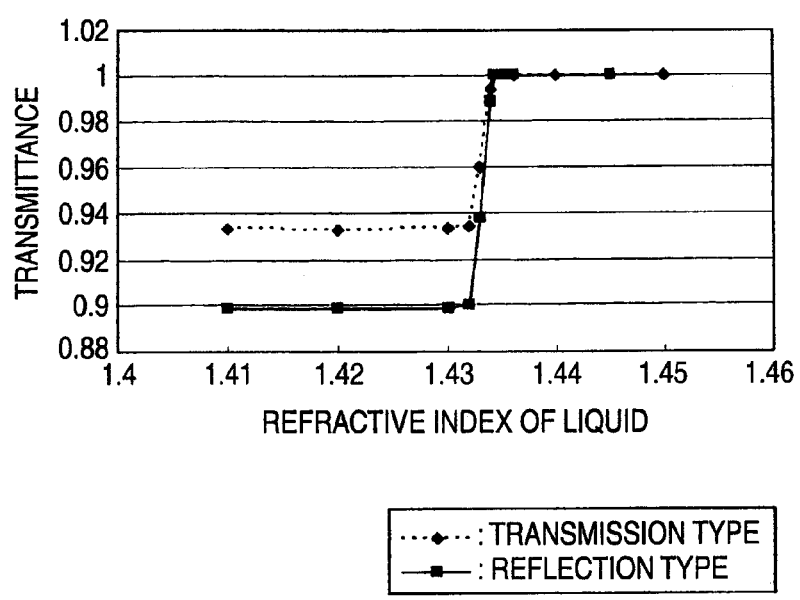
FIG. 29 is a graph showing the relationship between the refractive index and transmittance of liquid in the embodiment 14 of the present invention.

AS described above, in the construction that the reflecting means is provided to the optical fiber at the opposite side to the light source with respect to the grating-formed area, light is transmitted through the grating twice, and thus the sensitivity of the sensor is enhanced. FIG. 29 is a graph showing an example of the relationship between the refractive index of liquid and the transmittance in the reflection type construction in which the reflecting means is provided to the optical fiber at the opposite side to the light source with respect to the grating-formed area and the transmission type construction in which the reflecting means as shown in FIG. 23 is not provided. As shown in FIG. 29, it is apparent that the reflection type construction has a larger variation of transmittance with respect to the variation of the refractive index of liquid, and thus the variation of the refractive index can be more easily detected.

If a grating having the wavelength area of cladding-mode light in the wavelength area of Bragg reflection is used as the reflecting means, there would be achieved an effect of removing light serving as noise other than the cladding-mode light can be removed as in the case where the optical filter is inserted before the light receiving unit 3 in FIG. 7.

EMBODIMENT 15

Figure 30:
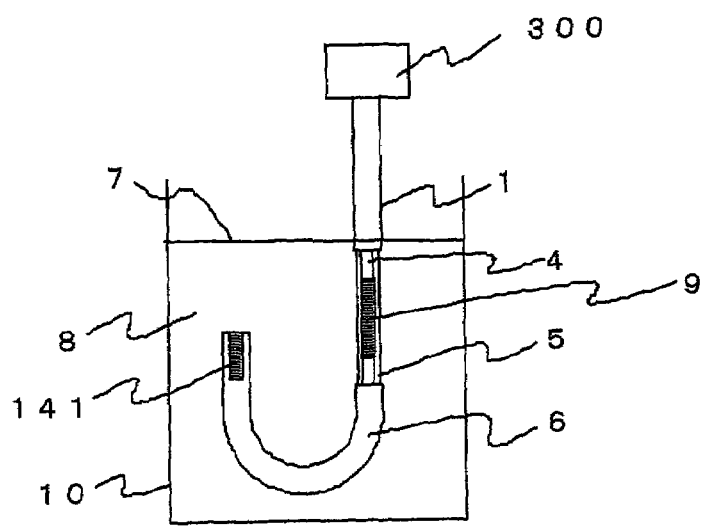
FIG. 30 is a schematic diagram showing the construction of an optical fiber sensor according to an embodiment 15 of the present invention and a method of using the same.

FIG. 30 is a schematic diagram showing the construction of an optical fiber sensor for detecting the property of liquid according to an embodiment 15 and a method of using the same. The light source 2, the optical fibers 142a, 142c, the circulator 142 and the light receiving unit 3 of FIG. 28 according to the embodiment 14 are replaced by an optical pickup 300. As described above, when the reflecting means is used, an optical pickup integrated with a light receiving element may be used in place of the method of providing the circulator to separate incident light and emission light from each other.

Figure 31:
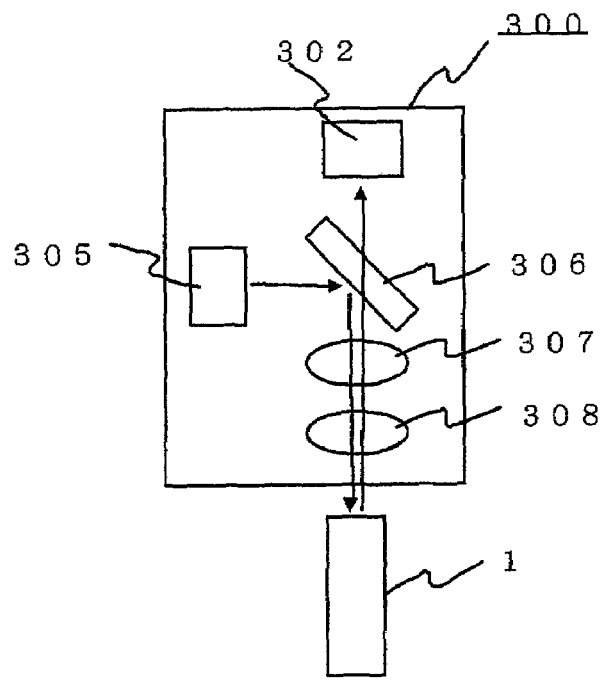
FIG. 31 is a schematic diagram showing the construction of an optical pickup 300 according to the embodiment 15 of the present invention.

FIG. 31 is a diagram showing the construction of the optical pickup 300. The optical pickup 300 is used for reading, writing, etc. of CD, and it is constructed by a light receiving element 302, a laser diode 305, a half mirror 306, a collimator lens 307, an objective lens 308, etc. Light from the laser diode 305 is reflected by the half mirror 306 so as to be incident to the optical fiber, and light emitted from the optical fiber is transmitted through the half mirror 306 and incident to the light receiving element 302. This is a simple construction in which the light incident to the optical fiber and the light emitted from the optical fiber are separated from each other by the half mirror 306. The respective elements are integrated in the optical pickup 300, whereby the optical pickup 300 can be constructed in a compact and light design. By constructing the connection parts between the optical fiber and the light source, the light receiving unit, etc. in a compact and light design, stress occurring at these portions under vibration-large environment can be reduced, and thus the reliability can be enhanced. The same effect can be achieved by replacing the light source 2, the optical fibers 142a, 142c, the circulator 142 and the light receiving unit 3 of the liquid level detecting optical fiber sensor according to the embodiment 7 by the optical pickup 300.

EMBODIMENT 16

Figure 32:
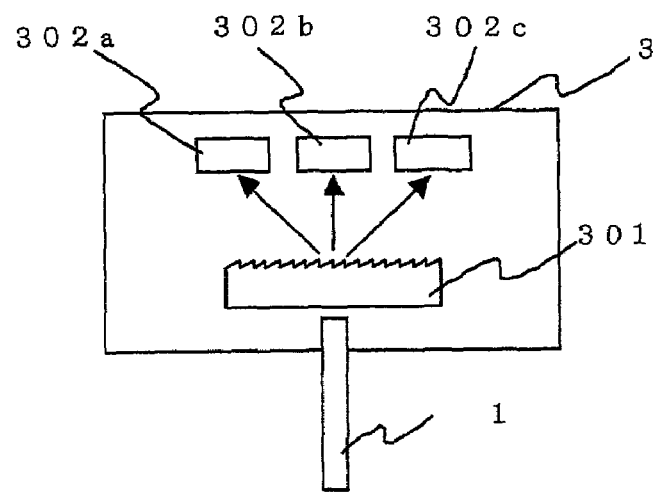
FIG. 32 is a schematic diagram showing the construction of a light receiving unit of an optical fiber sensor according to an embodiment 16 of the present invention.
Figure 33:
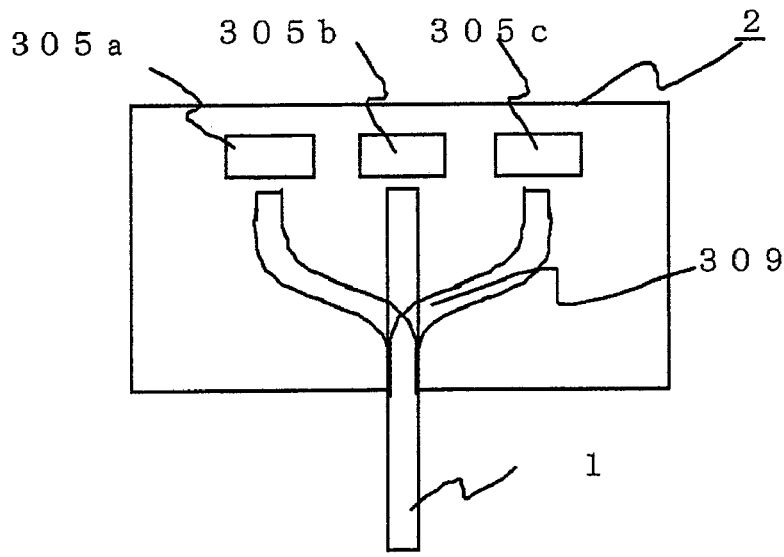
FIG. 33 is a schematic diagram showing the construction of a light source of an optical fiber sensor according to an embodiment 16 of the present invention.

FIG. 32 is a schematic diagram showing the construction of the light receiving unit of the liquid property detecting optical fiber sensor according to the embodiment 16. FIG. 33 is a diagram showing the construction of the light source of the liquid property detecting optical fiber sensor according to the embodiment 16. The liquid property detecting optical fiber sensor of the embodiment 16 is achieved by replacing the light receiving unit 3 of FIG. 23 of the embodiment 13 by the light receiving unit 3 of FIG. 32 and replacing the light source 1 by the light receiving unit 2 of FIG. 33.

The light receiving unit 3 of FIG. 32 is equipped with a diffraction grating 301 and three light receiving elements 302a, 302b, 302c. With respect to light emitted from the optical fiber 1, the travel direction thereof is changed in accordance with the wavelength of the light by the diffraction grating 301. The light receiving elements 302a, 302b, 302c are disposed at respective positions to which the cladding mode lights having different wavelengths travel respectively, and receive the cladding mode lights having the different wavelengths.

The light source 2 of FIG. 33 is equipped with a light multiplexing unit 309 for collecting input lights from three places into one light and outputting the one light, and three LDs 305a, 305b, 305c for generating lights of different wavelengths. Lights emitted from the three LDs are collected and made incident to the optical fiber 1 by the light multiplexing unit 309. The wavelengths of the lights emitted from the three LDs 305a, 305b, 305c are different cladding mode lights having different wavelength respectively, and they are made coincident with the wavelengths of lights detected by the three light receiving elements 302a, 302b, 302c. According to the above construction, the transmission light intensity of the grating for light beams of plural wavelengths can be detected.

Figure 34:
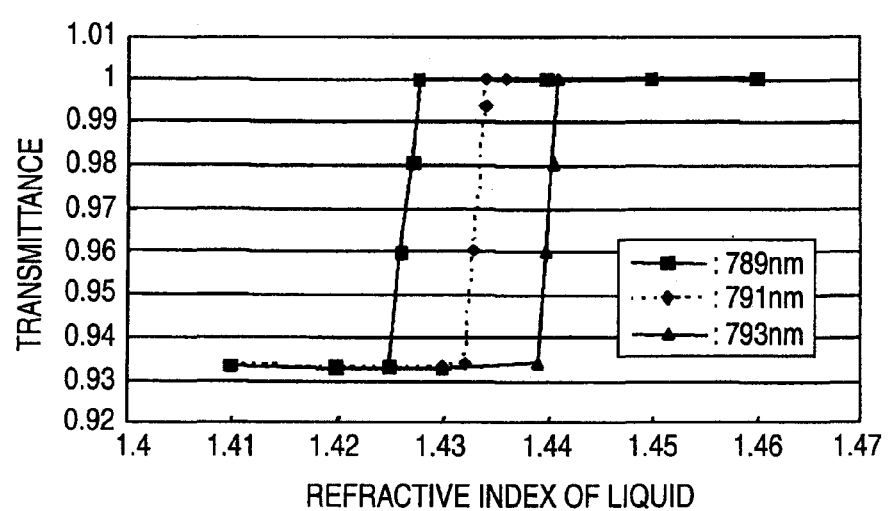
FIG. 34 is a graph showing the relationship between the refractive index and transmittance of liquid in the embodiment 16 of the present invention.

FIG. 34 is a graph showing an example of the transmittance when the refractive indexes of different kinds of liquid are detected by the three light receiving elements of the liquid property detecting optical fiber sensor according to the embodiment 16. To the transmittance is applied means of carrying out the comparison and calculation processing on the basis of the output values of the respective light receiving elements when the grating portion is immersed in liquid having a larger refractive index than the refractive index of the clad. The wavelength bands detected by three LDs and three light receiving elements are set to 789±0.2 nm, 791±0.2 nm and 793±0.2 nm, and each of the wavelengths contain one cladding-mode loss peak.

The cladding-mode loss peaks successively vanish from the lower wavelength side in connection with the increase of the refractive index of liquid. Therefore, if the wavelength of the input light is set to a low wavelength, the identifiable refractive index is lower. If the wavelength of the input light is set to a high wavelength, the identifiable refractive index is higher. Accordingly, as is apparent from FIG. 34, the refractive index of liquid whose transmittance sharply varies with respect to each wavelength exists.

The transmission light intensities of the cladding modes of plural wavelengths are detected by the construction described above, and thus the refractive indexes of liquid in a broader range than the embodiment 13 can be detected.

In the embodiment 16, three LDs are used as the light source, however, they may be replaced by a light emitting element having a broad wavelength band such as LED or the like.

Furthermore, means of displacing the light emitting timing of LD may be provided to the construction that the light source comprises plural LDs and the light receiving unit comprises one light receiving element, whereby the transmission light intensities of the respective wavelength bands of LDs are output successively in time from the light receiving element.

AS described above, the light emitting element having plural wavelength bands or plural light receiving elements for receiving light beams of different wavelength bands are provided, whereby the construction of detecting the transmission light intensities of the cladding modes of plural wavelength bands can be also implemented even in the case where the reflecting portion is formed at the tip of the optical fiber as shown in FIG. 28.

EMBODIMENT 17

Figure 35:
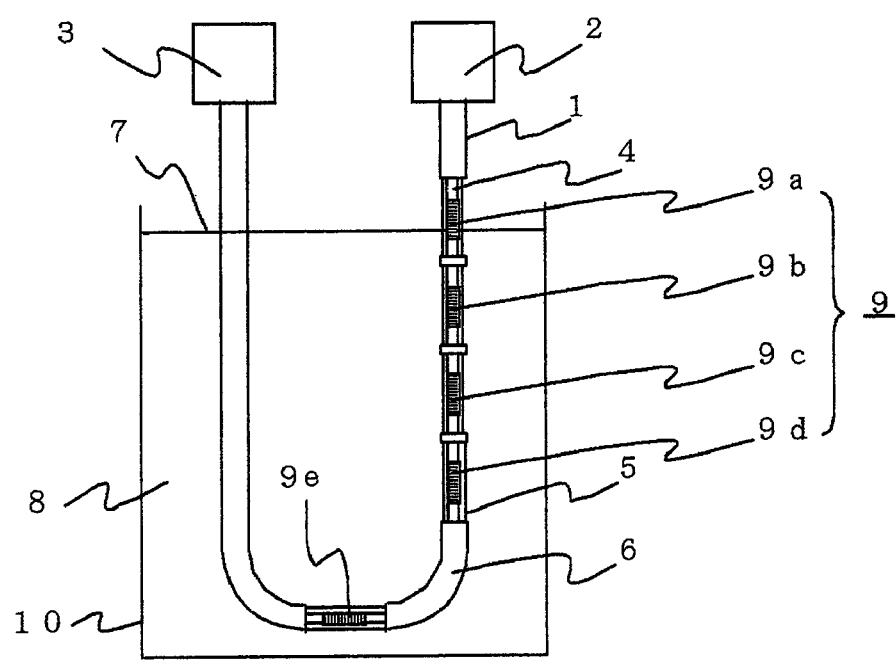
FIG. 35 is a schematic diagram showing the construction of an optical fiber according to an embodiment 17 of the present invention and a method of using the same.

FIG. 35 is schematic diagram showing the construction of an optical fiber sensor according to an embodiment 17 in which a liquid level detecting optical fiber sensor and a liquid property detecting optical fiber sensor are integrated with each other, and a method of using the same. This embodiment has the construction that the liquid level detecting optical fiber sensor to which the divisional gratings of the embodiment 6 are applied and the liquid property detecting optical fiber sensor of the embodiment 13 are combined with each other. The gratings 9a, 9b, 9c, 9d are liquid level detecting gratings, and they are required to be arranged in the variation direction of the liquid level. 9e represents a liquid property detecting grating and it can detect the liquid level while it is disposed in any direction with respect to the liquid level insofar as it is immersed in the liquid 8. The optical fiber 1 is bent in the neighborhood of the bottom surface of the container 10 for stocking the liquid 8, and the light source 2 and the light receiving unit 3 are disposed at the outside of the container 10. The grating 9e is disposed in the neighborhood of the bottom surface of the container 10, whereby the property of the liquid 8 can be measured irrespective of the amount of the liquid 8 in the container 10.

Figure 36:
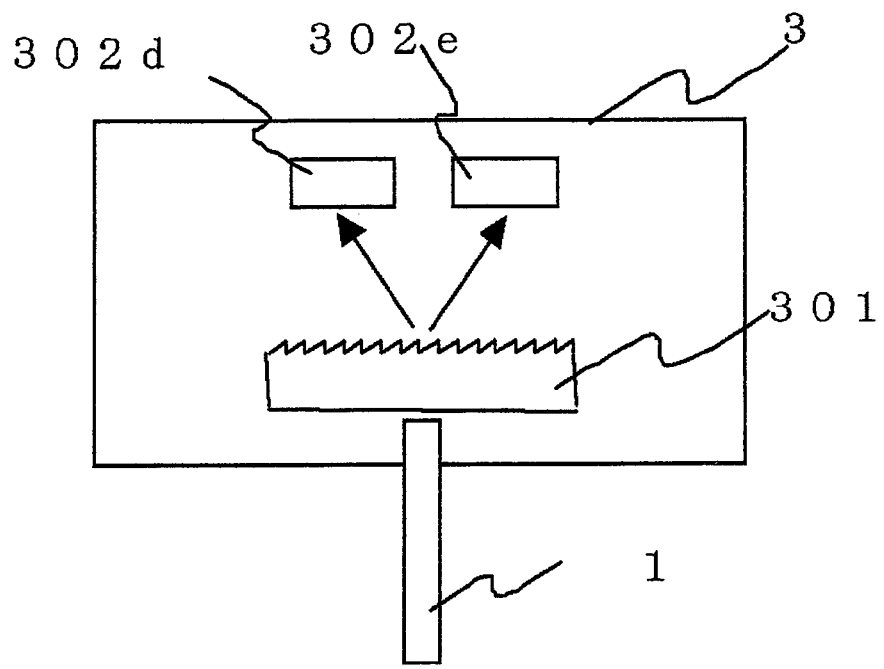
FIG. 36 is a schematic diagram showing the construction of a light receiving unit of an optical fiber sensor according to an embodiment 17 of the present invention.

In this embodiment, the variation of the liquid level and the variation of the liquid property are separated from each other, and thus the liquid level detecting optical fiber sensor and the liquid property detecting optical fiber sensor are constructed so as to detect transmission light intensities of different wavelengths. Therefore, a broad band element such as LED or the like is suitably used as the light source. FIG. 36 is a schematic diagram showing the construction of the light receiving unit 3 of the optical fiber sensor of the embodiment 17. A diffraction grating 301 is disposed so that light emitted from the optical fiber 1 is separated into light of wavelength area which detects the transmission loss of the liquid level detecting grating and travels to a light-level detecting light receiving element 302-1 and light of the wavelength area which detects the transmission loss of the liquid-property detecting grating and travels to a liquid-property detecting light receiving element 302-2.

In this case, the broad band LED is used as the light source, and the respective wavelengths are separated by the diffraction grating at the light receiving unit. However, light beams of LDs of different wavelengths may be multiplexed by a light multiplexer, demultiplexed by using a fiber type demultiplexer and then detected by the light receiving elements.

The grating period may be varied so that a cladding-mode appearing wavelength range is different between the liquid level detecting optical fiber sensor and the liquid property detecting optical fiber sensor.

Figure 37:
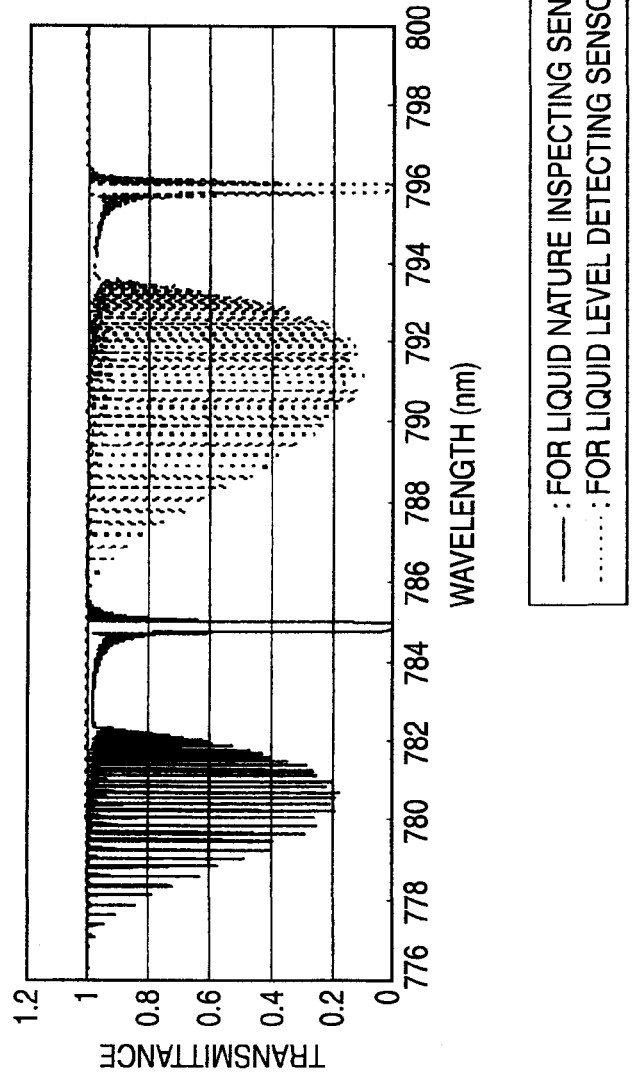
FIG. 37 is a graph showing the wavelength-dependency of the grating of the embodiment 17 according to the present invention.

The transmission light intensities of the grating with respect to light beams of two kinds of wavelengths corresponding to the liquid level detection and the liquid property detection can be detected. FIG. 37 is a graph showing the wavelength characteristic of the transmittance of the liquid level detecting grating and the liquid property detecting grating. The grating periods of the liquid level detecting grating and the liquid property detecting grating are set to 274 nm and 270 nm. As shown in FIG. 37, the respective cladding modes appear in different wavelength bands, and both the liquid level and the liquid property can be independently detected by using the light source of a wavelength around 790 nm for the detection of the liquid level and a wavelength around 780 nm for the detection of the liquid property. As described above, the grating periods corresponding to the liquid level detecting optical fiber sensor and the liquid property detecting optical fiber sensor are set to be different from each other, thereby achieving the construction that both the sensors can be formed in one optical fiber, so that the miniaturization and the reduction of the cost can be performed.

EMBODIMENT 18

The transmission light intensity of the cladding mode is varied in accordance with the difference of the refractive index of liquid, and thus the signal intensity which corresponds to the transmission light intensity and is output from the light receiving unit of the liquid level detecting optical fiber sensor is varied in accordance with the refractive index of liquid.

Therefore, in an embodiment 18, the embodiment 17 is provided with means for correcting the output signal intensity of the liquid level detecting optical fiber sensor on the basis of the output signal intensity of the liquid property detecting optical fiber sensor.

Figure 38:
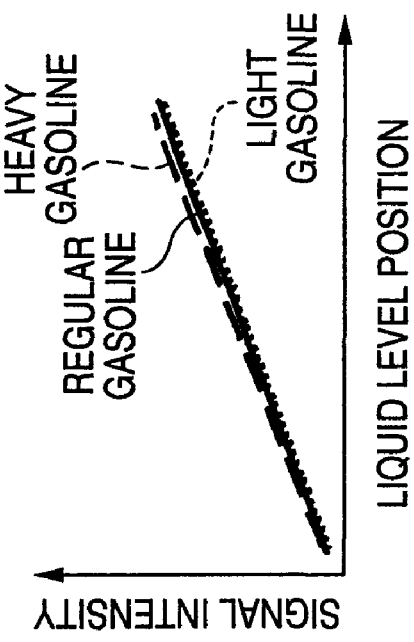
FIG. 38 is a graph showing the relationship between the output intensity of a light receiving unit before correction and the liquid level position in an embodiment 18 of the present invention.
Figure 38:
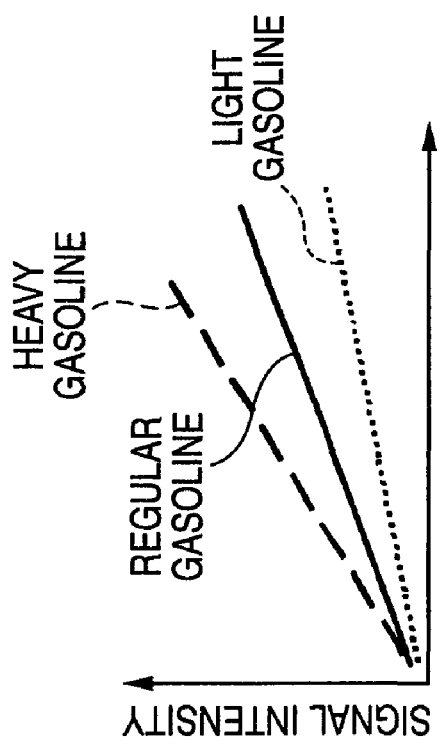

FIG. 38(a) is a graph showing the relationship between the output intensity of the light receiving unit of the liquid level detecting optical fiber sensor and the liquid level position for heavy gasoline, regular gasoline and light gasoline before correction in the embodiment 18. The refractive index of gasoline is slightly varied in accordance with the type of gasoline, and thus the relationship of the signal intensity to the liquid level position is varied as shown in FIG. 38(a). When the liquid level position is read, the achieved signal intensity is converted to the liquid level position, and thus the displacement of the signal intensity occurring when the refractive index of liquid varies becomes a measurement error.

In the embodiment 18, in addition to the construction of FIG. 35 and FIG. 36 of the embodiment 17, the output signal of a liquid level detecting light receiving element 302d and the output signal of a liquid property detecting light receiving element 302e are input to a liquid level correcting device, and the signal intensity of the liquid property detecting light receiving element 302-2 is corrected on the basis of the signal intensity of the liquid property detecting light receiving element 302e by the liquid level correcting device, and then the corrected signal intensity is output. A table of proportional coefficients used when the output signal intensity is corrected so that the output signal intensity representing the same liquid level is also achieved even in the case of liquid having a different refractive index is stored in a memory of the liquid level correcting device.

This table is achieved by achieving data as shown in FIG. 38(a) in advance and determining proportional constants from the relationship between the liquid level position and the signal intensity. For example, the proportional constant of heavy gasoline is represented by a, the proportional constant of regular gasoline is represented by b and the proportional constant of light gasoline is represented by c. In this case, the following calculation is made in the liquid level correcting device. For example, when the output signal of the liquid property detecting light receiving element 302e is judged to be equivalent to heavy gasoline in the liquid level correcting device, a is selected from the table and the achieved signal intensity of the liquid level detecting light receiving element 302d is multiplied by a. Likewise, if it is judged to be equivalent to regular gasoline, the achieved signal intensity is multiplied b. If it is judged to be equivalent to light gasoline, the achieved signal intensity is multiplied by c. Here, a, b, c beforehand represent the proportional coefficients with which the same liquid-level output signal is achieved for liquid having different refractive indexes by multiplication, and thus as shown in FIG. 38(b), the signal of the same signal intensity is output in the case of the same liquid level for different kinds of liquid having different refractive indexes from the liquid level correcting device. As described above, the optical fiber 1 is equipped with the area of the liquid property detecting grating 9e at the position where the optical fiber 1 is immersed in liquid, and the liquid level detecting gratings 9a, 9b, 9c, 9d at the positions at which the liquid traverses the optical fiber 1, and the light receiving unit is provided with the liquid property detecting light receiving element 302-2 for detecting the intensity of light of the wavelength area of the cladding mode of the grating 9e which is transmitted through the area where the liquid property detecting grating 9e is formed and the liquid level detecting light receiving element 302-1 for detecting the intensity of light of the wavelength of the cladding mode of the gratings 9a, 9b, 9c, 9d which is transmitted through the areas where the liquid level detecting gratings 9a, 9b, 9c, 9d are formed. Furthermore, the liquid level correcting device for outputting the signal representing the position of the liquid level on the basis of the signal intensity of the liquid property detecting light receiving element 302-2 and the output intensity of the liquid level detecting light receiving element 302-1 is provided. Therefore, the error of the liquid level position due to the difference of the refractive index can be reduced.

When the correction is performed, as shown in FIG. 35, it is unnecessary that the optical fiber for detecting the liquid level and the optical fiber for detecting the refractive index of liquid are constructed by one optical fiber, and the optical fiber sensor may be constructed so that they are constructed by different optical fibers.

With respect the other wavelength bands than that of this embodiment, the embodiment may be constructed by the light source of 1550 nm and the grating, for example.

EMBODIMENT 19

Figure 39:
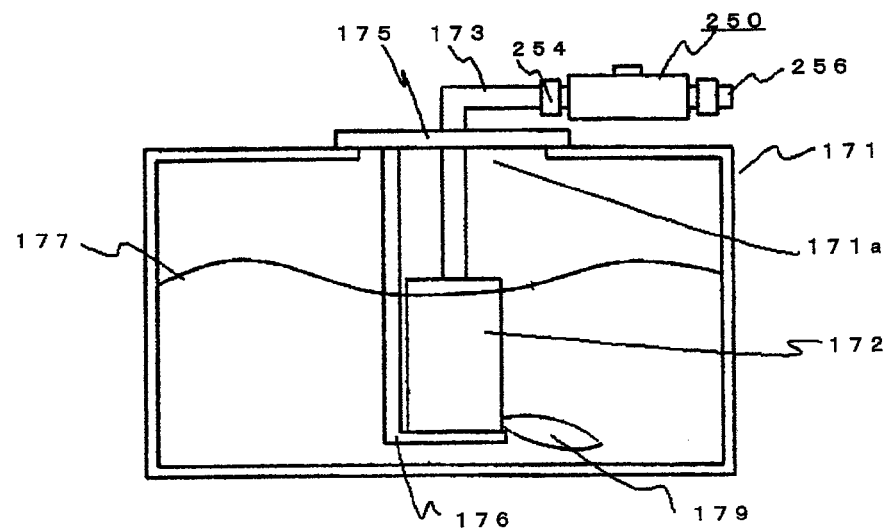
FIG. 39 is a schematic diagram showing a fixing state of an optical fiber sensor according to an embodiment 19 of the present invention.
Figure 40:
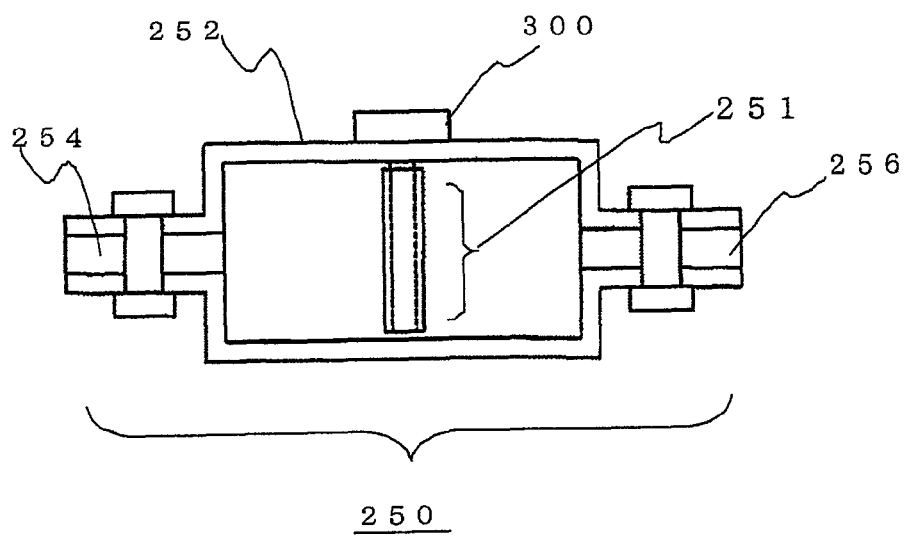
FIG. 40 is a schematic diagram showing the internal structure of an in-line liquid property detecting sensor according to the embodiment 19 of the present invention.

FIG. 39 is a schematic diagram showing the mounting state of a liquid property detecting optical fiber sensor disposed at the outside of the fuel tank according to an embodiment 19. A plate 175 having a fuel pump 172 and a discharge pipe 173 is disposed at the opening portion 171a of a fuel tank 171 for a vehicle. The fuel pump 172 is held to the plate 175 by a support member 176, and it is disposed so as to be immersed in the liquid level 177 of fuel. The liquid property detecting sensor is installed in an in-line liquid property detecting sensor 250. The in-line liquid property detecting sensor 250 is connected to the discharge pipe 173 at a fuel pump side inlet 254, and connected to a pipe, etc. connected to an injector for jetting fuel (not shown) a the injector side outlet 256. FIG. 40 is a diagram showing the internal construction of the in-line liquid property detecting sensor 250. In the in-line liquid property detecting sensor 250, an optical sensor probe 251 is inserted in a case 252 having the fuel pump side inlet 254 at one side and the injector side outlet 256 at the other side, and the optical pickup 300 constructed by the light source and the light receiving unit which are optically connected to the optical fiber of the optical sensor probe 251 is fixed to the outlet portion of the case 252 of the optical sensor probe 251. Here, the optical sensor probe 251 is shown in FIG. 30 of the embodiment 14. The grating 9 is formed at a part of the optical fiber 1, and the fiber jacket 6 at the portion of the grating 9 is removed so that the clad 5 of the optical fiber 1 at that portion is in contact with liquid of fuel. In FIG. 40, the case 252 is substantially filled with fuel, and thus the clad 5 in which the grating 9 is formed is in contact with fuel. Furthermore, according to the embodiment 19, the grating 141 for subjecting the wavelength area containing the wavelength of the loss peak of the cladding mode of the grating 9 to Bragg reflection is formed in the neighborhood of the end of the optical sensor probe 251 at the opposite side which is connected to the optical pickup 300. As shown in FIG. 23 of the embodiment 13, there may be a transmission structure in which the optical sensor probe 251 is not provided with any portion for reflecting the loss peak of the cladding mode and the light source 2 and the light receiving unit 3 are used in place of the optical pickup 300.

The fuel stocked in the fuel tank 171 is pumped up from the lower portion of the fuel pump 172 through the low-pressure side filter 179, and fed through the discharge pipe 173 to the injector of the engine during the operation of the engine. At this time, the fuel is passed around the optical sensor probe 251 of the in-line liquid property detecting sensor 250.

The liquid property detecting optical fiber sensor is installed in the above construction, and thus the refractive index of fuel can be detected. On the basis of the detected refractive index of the fuel, the other properties than the refractive index of the fuel, for example, the type of the fuel such as whether gasoline is light or heavy, or the composition of the fuel such as the alcohol concentration can be detected. At this time, the detection can be more easily performed by providing means for storing the relationship between the type and the refractive index of each fuel or the relationship between the composition and the refractive index of each fuel as a table in a memory in advance and comparing a detected refractive index with the table of the memory to output type or the composition of the fuel having the closest refractive index.

In the thus-constructed in-line liquid property detecting sensor 250, it is installed as a part of the fuel pipe and thus the optical sensor probe touches flowing fuel during the operation of the fuel pump. The surface of the fiber is cleaned by the fuel, and thus the characteristic as the sensor is hardly deteriorated, so that the property detection can be stably performed. Furthermore, the in-line liquid property detecting sensor 250 is connected between pipes, and it is easily detachable.

EMBODIMENT 20

In an embodiment 20, the optical sensor probe 251 as a part of the liquid property detecting optical fiber sensor is inserted in the fuel tank 171, and the optical pickup 300 connected to the optical sensor probe 251 is fixed to the outside of the fuel tank 171.

In the following description, plural examples indicating the mounting state of the liquid property detecting optical fiber sensor having the above construction will be described.

Figure 41:
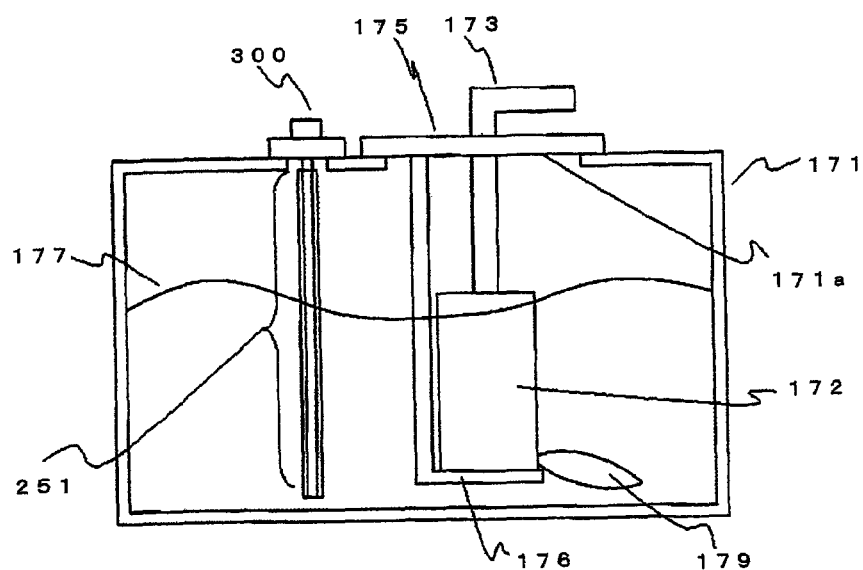
FIG. 41 is a schematic diagram showing a fixing state of an optical fiber sensor according to an embodiment 20 of the present invention.
Figure 42:
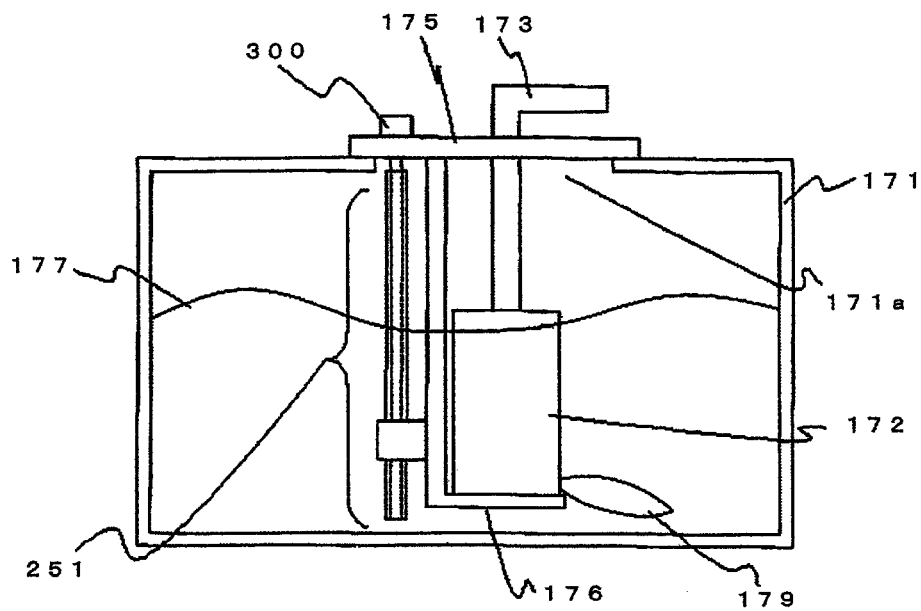
FIG. 42 is a schematic diagram showing the fixing state of the optical fiber sensor according to the embodiment 20 of the present invention.
Figure 43:
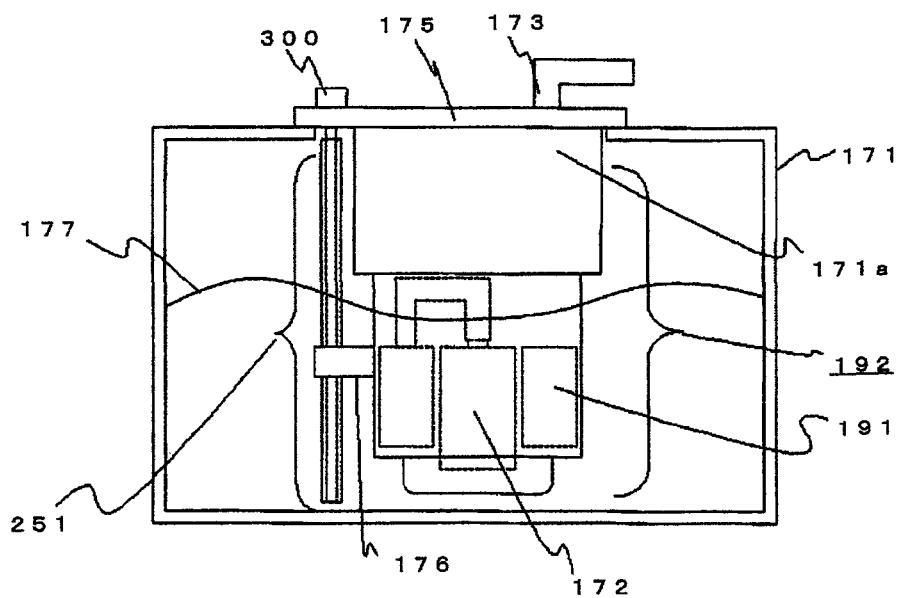
FIG. 43 is a schematic diagram showing the fixing state of the optical fiber sensor according to the embodiment 20 of the present invention.
Figure 44:
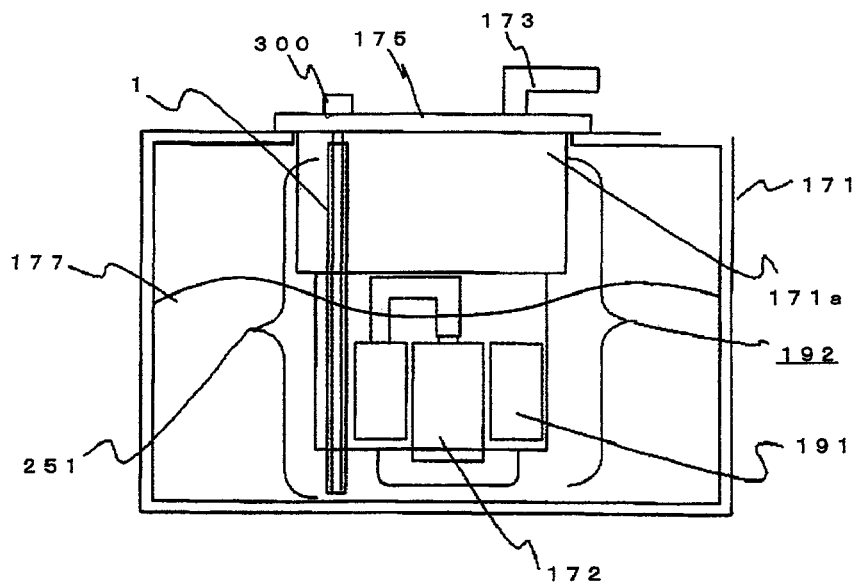
FIG. 44 is a schematic diagram showing the fixing state of the optical fiber sensor according to the embodiment 20 of the present invention.

FIG. 41 is a schematic diagram showing an example of the mounting state of the liquid property detecting optical fiber sensor disposed at a part of the fuel tank of the embodiment 20. FIG. 42 is a schematic diagram showing another example of the mounting state of the liquid property detecting optical fiber sensor disposed at a part of the fuel tank of the embodiment 20. FIG. 43 is a schematic diagram showing another example of the mounting state of the liquid property detecting optical fiber sensor disposed at a part of the fuel tank of the embodiment 20. FIG. 44 is a schematic diagram showing another example of the mounting state of the liquid property detecting optical fiber sensor disposed at a part of the fuel tank of the embodiment 20.

Under all the mounting state, the optical sensor probe 251 is inserted to be in the neighborhood of the bottom of the fuel tank 171, and the grating area formed in the optical sensor probe 251 is located in the neighborhood of the bottom of the fuel tank 171. Accordingly, the whole grating area is immersed in the fuel.

Under the mounting state shown in FIG. 41, the optical sensor probe 251 is inserted from a dedicated mounting hole at the upper portion of the fuel tank 171 so as to reach the neighborhood of the bottom portion of the fuel tank 171. The optical pickup 300 is fixed to the upper portion of a lid which closes the dedicated hole.

Under the mounting state shown in FIG. 42, the optical sensor probe 251 is inserted from a mounting hole formed in the plate 175 at the upper portion of the fuel tank 171 so as to reach the neighborhood of the bottom portion of the fuel tank 171. A part of the optical sensor probe 251 is held by a part of the support member 176 for holding the fuel pump 172 in the fuel tank 171. The optical pickup 300 is fixed to the upper portion of the mounting hole formed in the plate 175.

Under the mounting state shown in FIG. 43, the optical sensor probe 251 is inserted from a mounting hole formed in the plate 175 at the upper portion of the fuel tank 171 so as to reach the neighborhood of the bottom portion of the fuel tank 171. Furthermore, a part of the optical sensor probe 251 is held by a part of the fuel pump module 192 held by the plate 175 in the fuel tank 171. The optical pickup 300 is fixed to the upper portion of the mounting hole formed in the plate 175. The fuel pump module 192 includes the fuel pump 172 and the high-pressure side filter 191 at the fuel outlet side which are integrally provided.

Under the mounting state shown in FIG. 44, the optical sensor probe 251 is inserted from a mounting hole formed in the plate 175 at the upper portion of the fuel tank 171 so as to pass through a through hole in the fuel pump module 192 and reaches the neighborhood of the bottom portion of the fuel tank 171. A part of the optical sensor probe 251 extends from the bottom portion of the through hole to the bottom portion of the fuel tank, and a grating area is formed at this portion. The optical pickup 300 is fixed to the upper portion of the mounting hole formed in the plate 175.

By adopting any mounting state as described above, the attachment and detachment of the liquid property detecting optical fiber sensor to/from the tank can be easily performed. Under any mounting state, the grating-formed area is disposed at the bottom portion of the fuel tank, and thus the property of the fuel can be stably detected. Under the mounting states shown in FIGS. 42 to 44, the optical fiber is fixed together with the pump in the fuel tank, and thus the optical sensor probe 251 is hardly affected by fluidity of the fuel, so that the detection can be performed with high reliability.

EMBODIMENT 21

Figure 45:
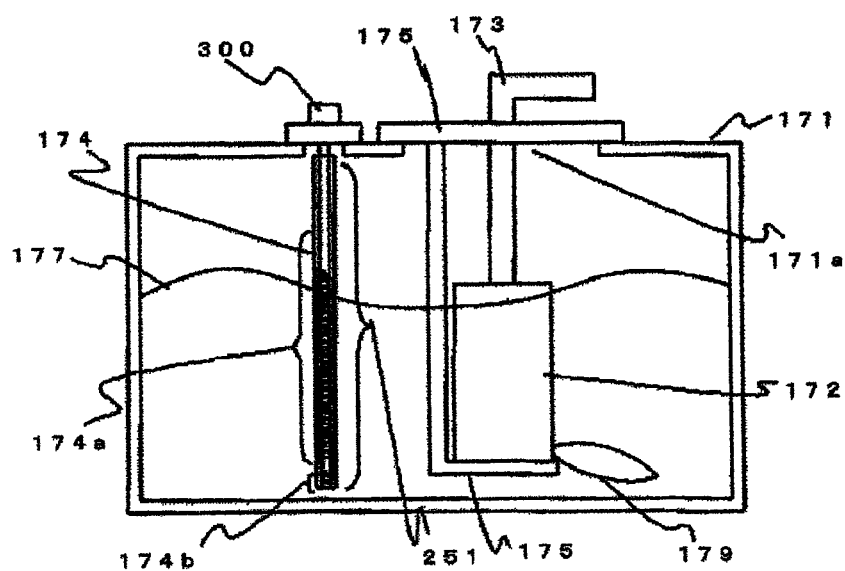
FIG. 45 is a schematic diagram showing the fixing state of an optical fiber sensor according to an embodiment 21 of the present invention.

FIG. 45 is a schematic diagram showing a mounting state of an optical fiber sensor according to an embodiment 21 in the fuel tank, the optical fiber sensor being achieved by forming the grating area of a liquid level detecting optical fiber sensor and the grating area of a property detecting optical fiber sensor in one optical fiber to thereby detect the liquid level and the property of liquid.

The optical sensor probe 251 is inserted from the opening portion at the upper portion of the fuel tank 171 so as to be in the neighborhood of the bottom. The optical pickup 300 is fixed to a lid for the opening portion, and the optical pickup 300 is connected to the optical sensor probe 251 for input/output light therebetween. A grating 174a for detecting liquid level and a grating 174b for detecting the property of liquid are formed in the optical sensor probe 251. The liquid level detecting grating 174a is disposed in the variation direction of the liquid level so that the liquid level 177 traverses the liquid level detecting grating 174a when the amount of gasoline in the fuel tank 171 varies. The liquid property detecting grating 174b is disposed so as to be near to the bottom portion of the fuel tank 171.

The liquid level detecting grating 174a and the liquid property detecting grating 174b have different grating periods so that the cladding modes thereof have different wavelength bands from each other. The optical pickup 300 is equipped with two light receiving elements disposed to receive light through a broad band light emitting element containing the wavelength of each cladding mode and a diffraction grating so that the transmission light intensities of the cladding mode of the liquid level detecting grating 174a and the cladding mode of the liquid property detecting grating 174b can be separately detected.

In the fuel gauge and the optical fiber sensor constructed as described above, the up and down shift of the liquid level 177 of gasoline can be detected on the basis of the transmission light intensity of the cladding mode of the liquid level detecting grating 174a, and further the property of gasoline can be detected on the basis of the transmission light intensity of the cladding mode of the liquid property detecting grating 174b even when the amount of gasoline is small. Furthermore, even when the precision of the liquid level is low because the property of gasoline is different, the height of the liquid level can be corrected on the basis of the property by providing the correcting means as in the case of the embodiment 18, thereby enhancing the precision of the liquid level.

As described above, the optical fiber sensor is equipped with the optical fiber which is equipped with the core and the clad having the grating-formed area and disposed so that at least a part of the grating-formed area is immersed in liquid, the light source for making light of the wavelength band of the cladding mode of the grating incident to the optical fiber and the light receiving unit for detecting the intensity of light which is incident from the light source to the optical fiber and transmitted through the grating-formed area. Therefore, the optical fiber sensor can be used as a sensor for detecting the liquid level or detecting the property of liquid by measuring the transmission light intensity of the cladding mode of the grating portion occurring due to the difference in refractive index between the clad and the liquid or between the clad and gas.

As described above, the detection is performed on the basis of the difference in refractive index between the optical fiber and the liquid or between the optical fiber and the gas. Therefore, even when the liquid level varies at all times due to vibration to the optical fiber or the like and thus the temperature difference between the gas-phase portion and the liquid-phase portion is moderate, the liquid level can be detected. Furthermore, there is not provided any portion at which the optical fiber is greatly narrowed through the fusing-drawing treatment or the like. Therefore, as compared with the method of forming a narrow portion in the optical fiber, the mechanical strength is large and the level liquid or the property of liquid can be detected with high reliability under even a large vibration environment.

As described above, the liquid level detecting optical fiber sensor and the liquid property detecting optical fiber sensor carry out the detecting operation on the basis of the same basic principle of using the relationship between the refractive index of the outside of the clad at the grating-formed portion and the transmission characteristic of the cladding mode. Accordingly, they may be used while interchanged by each other.

Furthermore, in the above embodiments, the transmission light intensity based on the magnitude of the loss peak of the cladding mode is detected by the light receiving unit. However, the transmission light intensity of light of the wavelength band between the loss peak of the cladding mode and the loss peak of the neighboring wavelength may be detected. As is apparent from FIG. 5 showing the transmission spectrum of the liquid level detecting optical fiber sensor, there is a tendency that the transmittance of light of the wavelength band between the loss peak and the loss peak of the neighboring wavelength is gradually lower as the loss peak is smaller. Therefore, the relationship between the position of the liquid level or the refractive index of liquid and the transmission light intensity has the opposite tendency to the case where the transmission intensity of the wavelength band containing the loss peak is detected. However, the detection of the liquid level and the detection of the refractive index of liquid can be performed by detecting the transmission light intensity of light of the wavelength band between the loss peak and the loss peak of the neighboring wavelength.

EMBODIMENT 22

A liquid property detecting optical fiber sensor of an embodiment 22 has basically the same construction as the liquid property detecting optical fiber sensor of the embodiment 13, and also further has a construction that the light source 2 comprises LED having a broader light emission wavelength area than the wavelength band of the cladding mode in which a loss peak caused by a cladding mode appears and the light receiving unit 3 comprises a photodiode for detecting the light intensity of the whole of a broader wavelength area than the wavelength band of the cladding mode. Accordingly, the light emission wavelength area of the light source 2 and the detecting wavelength area of the light receiving unit 3 are broader than the wavelength band of the cladding mode of the grating. The light emission wavelength of LED is set to a wavelength in the 800 nm band, and the optical fiber 1 being used is set so that the core of about 2 microns in diameter has a single mode in the 800 nm band, and the difference in refractive index between the core and the clad is equal to about 2%.

Figure 46:
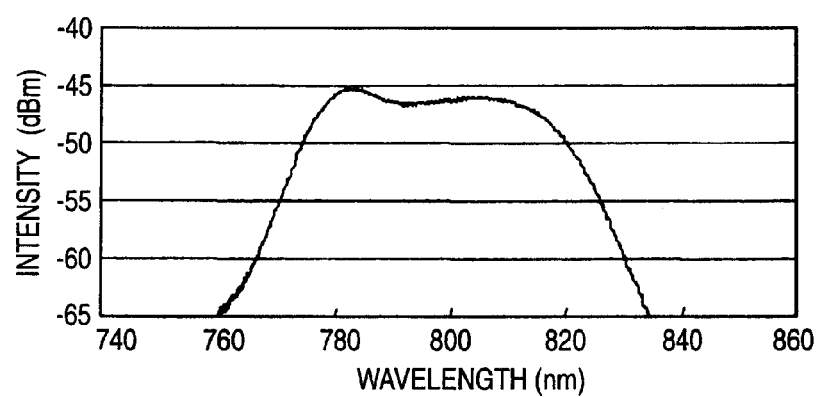
FIG. 46 is a graph showing the characteristic of a light source of an optical fiber sensor according to an embodiment 22 of the present invention.

FIG. 46 is a graph showing the light emission spectrum of the light source 2 of the embodiment 22. The light source 2 has a light emission wavelength area in the range from 775 nm to 815 nm in which the center wavelength is set to 795 nm and the half bandwidth is set to about 40 nm. In this light source 2, the light output at the wavelength which provides the largest light intensity is equal to −45 dBm, and the light power of the whole light emission wavelength area is smaller than 1 mW. By setting the light output to less than 1 mW, the temperature of liquid is prevented from being increased by light of cladding mode scattering to the liquid side.

Figure 47:
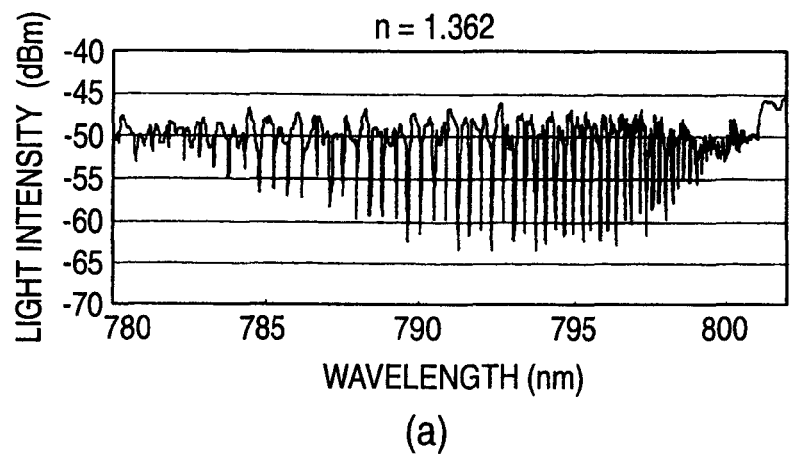
FIG. 47 is a graph showing the characteristic of the grating of the optical fiber sensor of the embodiment 22 of the present invention.
Figure 47:
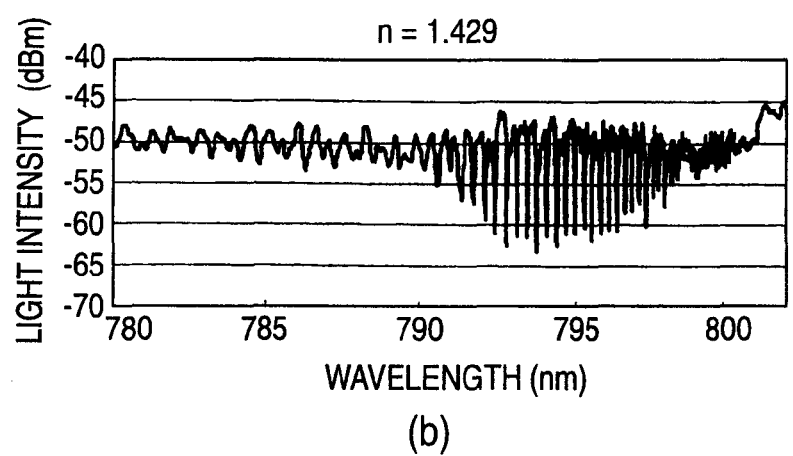
Figure 47:
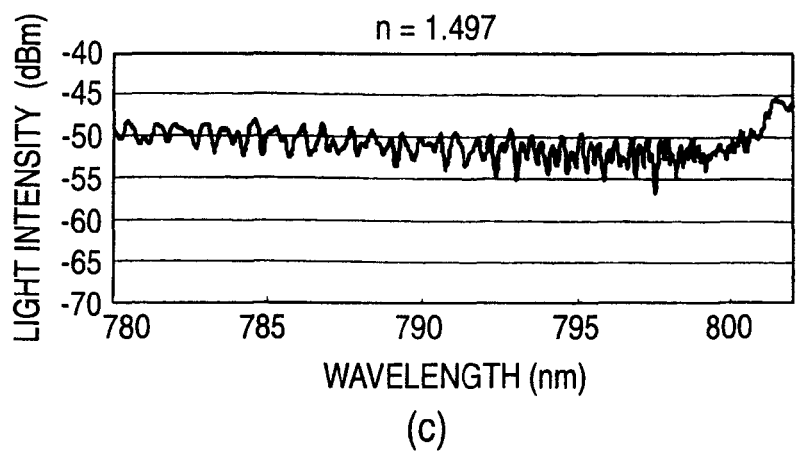

FIG. 47(a) is a graph showing the spectrum of light which is incident from the light source 2 into the optical fiber 1, passed through the grating 9 and then emitted to the light receiving unit 3 side when liquid of 1.362 in refractive index is brought into contact with the periphery of the clad 5 in which the grating 9 is formed. When the surrounding of the clad 5 is air, substantially the same spectrum as shown in FIG. 47(a) is achieved, and this spectrum has little variation when it comes into contact with liquid having a refractive index of 1.362 or less. As shown in FIG. 47(a), the wavelength band of the cladding mode of the grating 9 corresponds to an area from about 780 nm to about 800 nm. Accordingly, the light emission wavelength area of the light source 2 is broader than the wavelength band of the cladding mode, and contains the whole wavelength area of the cladding mode concerned. Furthermore, the optical fiber 1 in which the difference in refractive index between the core and the clad is relatively larger, that is, about 2% is used, and thus the photo-induced refractive-index variation of the core when the grating is formed can be increased. The grating of the embodiment 22 is designed as a grating in which the coupling from the propagation mode in the core to the cladding mode is increased by using the optical fiber having the large difference in refractive index between the core and the clad so that the loss peak of the cladding mode is magnified, for example, so that the transmittance of light of the loss peak is reduced to ¹⁄₁₀ or less of the transmittance between the neighboring loss peaks in the neighborhood of the center of the wavelength band of the cladding mode.

FIGS. 47(b) and (c) are graphs showing the optical spectra detected at the light receiving side when liquid of 1.429 and 1.497 in refractive index is brought into contact with the periphery of the clad 5 in which the grating 9 is formed. The optical spectrum varies so that the absorption peak at the short wavelength side is vanishing as the refractive index of the liquid in contact with the clad 5 is larger. On the other hand, the transmittance between the neighboring absorption peaks is gradually reduced as the refractive index of the liquid in contact with the clad 5 is larger.

Figure 48:
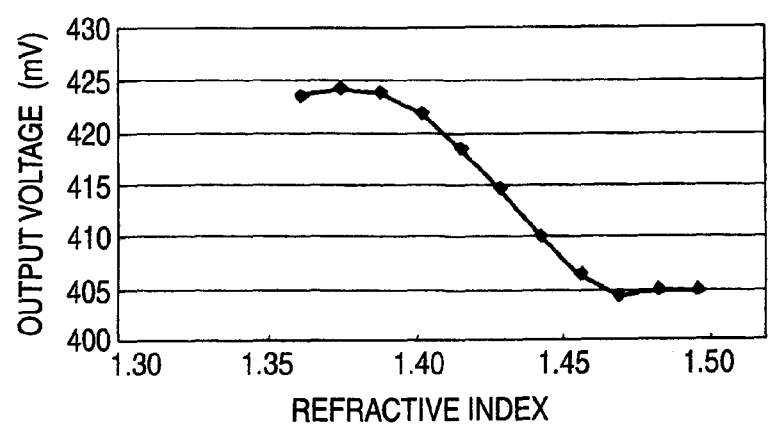
FIG. 48 is a graph showing the characteristic of the optical fiber sensor according to the embodiment 22 of the present invention.

The light intensity detected by the light receiving unit 3 is affected by the variation of the transmittance of the whole light emission wavelength area of LED of the grating 9 which corresponds to the refractive index of the liquid in contact with the clad 5. FIG. 48 is a graph showing the relationship between the refractive index of the liquid in contact with the clad 5 and the output voltage of the photodiode of the light receiving unit 3. The output voltage is little varied when the refractive index of the liquid is in the range from 1.36 to 1.39 and in the range from 1.47 to 1.50, however, the output voltage is lowered as the refractive index increases when the refractive index is in the range from 1.39 to 1.47. This shows that the loss peak inherent to the cladding mode disappears and the transmittance between the neighboring absorption peaks is reduced with the increase of the refractive index of the liquid, so that the transmittance of the whole wavelength area of the cladding mode of the grating 9 is lowered. As described above, the output voltage of the light receiving unit 3 is varied in accordance with the variation of the refractive index of the liquid in contact with the clad 5. Therefore, the variation of the refractive index of the liquid in contact with the clad 5 can be detected by detecting the output voltage of the light receiving unit 3.

The above phenomenon that the transmittance of the whole wavelength area of the cladding mode is lowered when the refractive index of the liquid in contact with the clad 5 is higher is considered to be remarkable because the grating of the embodiment 22 is formed by using the optical fiber 1 having a relatively large refractive index difference of about 2% so that the photoinduced refractive index variation of the core is increased.

The optical fiber sensor of the embodiment 22 is used as the liquid property detecting optical fiber sensor. However, it can be used as the liquid level detecting optical fiber sensor with the same construction by disposing the grating-formed area at such a position that the liquid level traverses the grating-formed area when the liquid level varies.

The light emission wavelength area of the light source 2 and the detecting wavelength area of the light receiving unit 3 are broader than the wavelength band of the cladding mode of the grating as in the case of the embodiment 22, thereby achieving the optical fiber sensor which is simple in construction and hardly affected by an environmental variation of temperature, vibration or the like.

The construction of the embodiment 22 may be combined with the construction of another embodiment, and for example, the reflecting means may be provided to one terminal of the optical fiber 1 as in the case of the embodiments 7 and 14, for example. In this case, the reflecting means may be formed of a reflecting grating in which a partial area of the wavelength area of the cladding mode is set to the wavelength area of Bragg reflection, whereby the detection sensitivity in that wavelength area can be enhanced.

The short-period grating described above is used as the grating used in the embodiments 1 to 22. In the short-period grating, the wavelength of the loss peak of the cladding mode little varies, and the magnitude of the peak varies even when the refractive index of liquid in contact with the clad varies. Therefore, it is unnecessary to provide means for estimating the wavelength shift of the peak, and the liquid level position of liquid and the property of the liquid can be detected by detecting the transmitted light intensity, so that the construction is simple.

The invention claimed is:

1. An optical fiber sensor, comprising:
   an optical fiber that includes a core having an area with a grating formed thereon and a clad, the optical fiber being disposed so that the whole of the area with the grating is immersed in fuel in a fuel tank;
   a light source for making light incident to the optical fiber so that a cladding mode light having a wavelength band is generated by the grating; and
   a light receiving unit for detecting an intensity of the light incident from the light source to the optical fiber and transmitted through the area with the grating, whereby a property of the fuel is detected.

2. The optical fiber sensor according to claim 1, wherein the area with the grating is disposed in a case having an inlet to which fuel is fed in and an outlet of the fuel, and the light source and the light receiving unit are fixed to the outside of the case.

3. The optical fiber sensor according to claim 1, wherein the area with the grating is disposed at the bottom portion of the fuel tank.

4. An optical fiber sensor, comprising:
   an optical fiber that includes a core have an area with a grating formed thereon and a clad, the optical fiber being disposed so that the whole of the area with the grating is immersed in fuel in a fuel piping;
   a light source for making light incident to the optical fiber so that a cladding mode light having a wavelength band is generated by the grating; and
   a light receiving unit for detecting an intensity of the light indecent from the light source to the optical fiber and transmitted through the area with the grating, whereby a property of the fuel is detected.

5. An optical fiber sensor, comprising:
   an optical fiber that includes a core having an area with a grating formed thereon and a clad, the optical fiber being disposed so that at least a part of the area with the grating formed is immersed in liquid, wherein the area with the grating is disposed at a position at which the liquid level traverses the area with the grating when the liquid level varies and the liquid level is detected;

a light source for making light incident to the optical fiber so that a cladding mode light having a wavelength band is generated by the grating; and a light receiving unit for detecting an intensity of the light incident from the light source to the optical fiber and transmitted through the area with the grating.

6. The optical fiber sensor according to claim 5, wherein the light receiving unit includes plural light receiving elements for receiving light of different wavelengths, whereby the intensities of the cladding mode light having different wavelengths transmitted through the grating are detected.

7. The optical fiber sensor according to claim 5, wherein the area with the grating is divided into plural portions.

8. The optical fiber sensor according to claim 5, wherein the surface of the clad in the area with the grating is subjected to a coating having a larger wettability angle to the liquid than the clad.

9. The optical fiber sensor according to claim 5, wherein the optical fiber has a first area with a first grating formed therein, the first that area with the first grating being disposed so that the whole of the first area is immersed in liquid, and a second area with a second grating formed therein, the second area with the second grating being disposed so that the liquid level traverses the second area when the liquid level of the liquid varies, and the light receiving unit has a first light receiving element for detecting the intensity of a light of a wavelength area of a cladding mode at the first grating which is transmitted through the first area with the first grating and a second light receiving element for detecting the intensity of light of a wavelength area of a cladding mode at the second grating which is transmitted through the second area with the second grating.

10. The optical fiber sensor according to claim 9, wherein the wavelength area of the cladding mode at the first grating and the wavelength areas of the cladding mode at the second grating are different from each other.

11. The optical fiber sensor according to claim 9, further comprising means for outputting a signal representing the position of the liquid level on the basis of the signal intensity of the first light receiving element and the signal intensity of the second light receiving element.

12. The optical fiber sensor according to claim 5, wherein an optical wavelength filter having a transmission area in a wavelength area of the cladding mode is disposed between the light receiving unit and the optical fiber.

13. The optical fiber sensor according to claim 5, further comprising an optical circulator between the light receiving unit and the optical fiber.

14. The optical fiber sensor according to claim 1, wherein the optical fiber is fixed in a fuel tank together with a fuel pump.

15. The optical fiber sensor according to claim 5, wherein the light source is disposed so that light from the light source is incident to one end of the optical fiber, the light receiving unit is disposed so as to detect the intensity of light emitted from the one end, and reflecting means for reflecting the light the wavelength band of the cladding mode passing through the area with the grating is disposed at the opposite side to the one end of the optical fiber.

16. The optical fiber sensor according to claim 15, wherein the reflecting means is an another grating having a wavelength band of Bragg reflection, and the wavelength band of Bragg reflection contains the wavelength of the cladding mode passing through the area with the grating.

17. The optical fiber sensor according to claim 15, further comprising an optical circulator, wherein the one end of the optical fiber, the light source and the light receiving unit are connected to different ports of the optical circulator.

18. The optical fiber sensor according to claim 15, wherein the light source and the light receiving unit are constructed by an optical pickup in which the light source and the light receiving unit are integrated.

19. The optical fiber sensor according to claim 5, wherein a light emission wavelength area of the light source and a detecting wavelength area of the light receiving unit are broader than the wavelength band of the cladding mode at the grating.

20. The optical fiber sensor according to claim 5, wherein the light source includes plural light emitting elements for emitting light of different wavelengths, whereby the intensities of the cladding mode light having different wavelengths transmitted through the grating are detected.

* * * * *